United States Patent
Fabrikant

(10) Patent No.: US 9,510,747 B2
(45) Date of Patent: Dec. 6, 2016

(54) SYSTEM AND METHOD FOR OPHTHALMIC SURFACE MEASUREMENTS BASED ON OBJECTIVE QUALITY ESTIMATION

(71) Applicant: AMO Development, LLC, Santa Ana, CA (US)

(72) Inventor: Anatoly Fabrikant, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 449 days.

(21) Appl. No.: 13/796,513

(22) Filed: Mar. 12, 2013

(65) Prior Publication Data

US 2013/0204237 A1 Aug. 8, 2013

Related U.S. Application Data

(63) Continuation-in-part of application No. 13/690,979, filed on Nov. 30, 2012, now abandoned.

(60) Provisional application No. 61/565,436, filed on Nov. 30, 2011.

(51) Int. Cl.

| | |
|---|---|
| *A61B 3/00* | (2006.01) |
| *A61F 9/008* | (2006.01) |
| *A61B 3/107* | (2006.01) |
| *A61B 5/107* | (2006.01) |

(52) U.S. Cl.
CPC ............ *A61B 3/0025* (2013.01); *A61B 3/107* (2013.01); *A61F 9/00804* (2013.01); *A61B 5/1077* (2013.01); *A61F 9/00806* (2013.01); *A61F 2009/0088* (2013.01); *A61F 2009/00872* (2013.01); *A61F 2009/00882* (2013.01)

(58) Field of Classification Search
CPC .... A61B 3/107; A61B 5/725; A61B 3/0025; A61B 5/1077; A61F 9/0804; A61F 9/00806; A61F 2009/00872; A61F 2009/0088; A61F 2009/00882
See application file for complete search history.

(56) References Cited

U.S. PATENT DOCUMENTS

| | | | |
|---|---|---|---|
| 2002/0099282 A1* | 7/2002 | Knobbe et al. | 600/365 |
| 2007/0091263 A1* | 4/2007 | Chernyak et al. | 351/205 |
| 2013/0138094 A1 | 5/2013 | Fabrikant | |

OTHER PUBLICATIONS

Schweigerling, J. et al., "Using corneal height maps and polynomial decomposition to determine corneal aberrations," Opt. Vis. Sci., vol. 74, No. 11 (1997).*
Bierman, G. J., *Factorization Methods for Discrete Sequential Estimation.* New York: Academic Press, 1977. Two title pages and pp. 18-21.
Spiesberger, J. L., et al. "Mapping Climatic Temperature Changes in the Ocean with Acoustic Tomography: Navigational Requirements." *Institute of Electrical and Electronic Engineers Journal of Ocean Engineering*, vol. 22, No. 1, (1997): pp. 128-142.

* cited by examiner

*Primary Examiner* — Gary Jackson
*Assistant Examiner* — Scott T Luan
(74) *Attorney, Agent, or Firm* — Abbott Medical Optics Inc.

(57) ABSTRACT

Systems and methods for measuring a topography of an optical tissue surface of an eye are provided by combining a measured elevation of the surface with a priori information of the surface to provide an estimate of mean and covariance of post-measurement orthogonal polynomial sequence amplitudes associated with the surface, determining a variance of elevation of the surface from the estimate, and constructing the topography from the estimate of mean and covariance of post-measurement amplitudes based on a comparison of the variance of elevation of the surface with a pre-determined threshold. The a priori information includes an estimate of mean and covariance of pre-measurement orthogonal polynomial sequence amplitudes associated with the surface.

12 Claims, 31 Drawing Sheets

SYSTEM AND METHOD FOR OPHTHALMIC SURFACE MEASUREMENTS BASED ON OBJECTIVE QUALITY ESTIMATION

CROSS-REFERENCES TO RELATED APPLICATIONS

This application is a continuation-in-part of U.S. patent application Ser. No. 13/690,979 filed Nov. 30, 2012, which claims the benefit of priority to U.S. Patent Application No. 61/565,436 filed Nov. 30, 2011. The content of each of these filings is incorporated herein by reference.

BACKGROUND OF THE INVENTION

Embodiments of the present invention relate generally to surface measurements of an eye and more particularly, to corneal topography or wavefront measurements of the eye based on estimation.

Known laser eye surgery procedures generally employ an ultraviolet or infrared laser to remove a microscopic layer of stromal tissue from the cornea of the eye. Examples of laser eye surgery procedures include photorefractive keratectomy (PRK), phototherapeutic keratectomy (PTK), laser assisted in situ keratomileusis (LASIK), laser epithelial keratomileusis (LASEK), and the like. A laser typically removes a selected shape of a corneal tissue, often to correct refractive errors of an eye. Ultraviolet laser ablation results in photo-decomposition of a corneal tissue, but generally does not cause significant thermal damage to adjacent and underlying tissues of an eye. Irradiated molecules are broken into smaller volatile fragments photochemically, directly breaking intermolecular bonds.

Laser ablation procedures can remove a targeted amount of corneal stroma to change the corneal contour for varying purposes, such as for correcting myopia, hyperopia, astigmatism, and the like. Control over a distribution of ablation energy across a cornea may be provided by a variety of systems and methods, including use of ablatable masks, fixed and moveable apertures, controlled scanning systems, eye movement tracking mechanisms, and the like. In known systems, a laser beam often comprises a series of discrete pulses of laser light energy, with a total shape and amount of tissue removed being determined by a shape, size, location, and/or number of laser energy pulses impinging on the cornea. A variety of algorithms may be used to calculate the pattern of laser pulses used to reshape the cornea so as to correct a refractive error of an eye. Known systems make use of a variety of forms of lasers and laser energy to effect a correction, including infrared lasers, ultraviolet lasers, femtosecond lasers, wavelength multiplied solid-state lasers, and the like. Alternative vision correction techniques make use of radial incisions in a cornea, intraocular lenses, removable corneal support structures, and the like.

Known corneal correction treatment methods have generally been successful in correcting standard vision errors, such as myopia, hyperopia, astigmatism, and the like. By customizing an ablation pattern based on wavefront measurements, it has been possible to correct minor aberrations so as to reliably and repeatedly provide visual acuity greater than 20/20. Such detailed corrections benefit from an extremely accurate ablation of tissue.

Known methods for calculation of a customized ablation pattern using wavefront sensor data generally involves mathematically modeling a surface of the cornea using expansion series techniques. More specifically, Zernike polynomials have been employed to model the corneal surface and refractive aberrations of the eye. Coefficients of a Zernike polynomial are derived through known fitting techniques, and an optical correction procedure is then determined using a shape indicated by a mathematical series expansion model.

More recently, refractive correction treatments have considered combining corneal topography measurement data with wavefront measurements to determine the ablation pattern. Conventional corneal topography measurements are typically noisy and can include gaps in the measured field. Wavefront aberrometers and other in vivo ophthalmic measurement devices often face the same problem. The full image derived from such devices can be restored by decomposing available data into Zernike series or any other orthogonal basis functions. However, the accuracy of such decomposition, depending on the measurement noise level and the sample size of available data, needs to be evaluated. Oftentimes, there is a need to optimally combine several arbitrary sets of measurement data together with a priori information about the measured field.

For example, corneal or wavefront data acquired by medical diagnostics devices, such as the WaveScan® aberrometer by Abbott Medical Optics Inc. or the Atlas™ corneal topographer by Carl Zeiss Meditec, Inc., are typically converted to a two-dimensional field by known interpolation scheme or through decomposition of available data into Fourier or orthogonal polynomials with subsequent reconstructions of the two-dimensional field from those decompositions.

Hence, although current approaches provide benefits to patients in need thereof, there continues to be a need for improved ophthalmic measurement data techniques, particularly for refractive correction. Embodiments of the present invention provide solutions for at least some of these outstanding needs.

BRIEF SUMMARY OF THE INVENTION

Embodiments of the present invention encompass systems and methods for objective quality estimation for wavefront and corneal topography measurements. Such techniques are particularly useful in situations where ocular wavefront measurements and/or corneal topography measurements may contain mostly measurement data or present gapped coverage area. Relatedly, embodiments of the present invention encompass techniques for restoring full measured fields. Further, embodiments of the present invention encompass systems and methods for providing an objective estimate of the measurement quality. For example, embodiments provide for the generation of an uncertainty map which can be compared or correlated with a restored measured field.

In one aspect, embodiments of the present invention encompass systems and methods for evaluating a topography of a corneal surface of an eye of a patient. Exemplary methods may include measuring an elevation field for the patient eye corneal surface, determining a measured Zernike amplitude profile for the patient eye based on the elevation field, and combining the measured Zernike amplitude profile with a priori corneal surface information to provide an estimated Zernike amplitude profile and an estimated Zernike amplitude covariance matrix for the patient eye. In some instances, the a priori corneal surface information can include mean and covariance Zernike amplitude profiles associated with multiple corneal surfaces of a general population. In some instances, methods may further include constructing a corneal topography map for the patient based on the estimated Zernike amplitude profile, constructing a corneal topography uncertainty map for the patient based on the estimated Zernike covariance matrix, and evaluating the patient corneal surface topography based on the corneal topography map and the corneal uncertainty map. According to some embodiments, the measured Zernike amplitude profile for the patient eye is determined by decomposing the elevation field of the patient eye corneal surface into a Zernike series representation. In some instances, the a priori corneal surface information is obtained by acquiring individual topography elevation fields corresponding respectively to individual eyes of the general population, decomposing the individual topography elevation fields into corresponding a Zernike series representations, evaluating a mean and a variance of amplitudes of the Zernike series representations, and preparing the a priori information from the mean and the variance of amplitudes of the Zernike series representations. In some instances, the combining step includes inputting the a priori information into a Kalman-Bucy filter together with the measured Zernike amplitude profile. In some instances, the inputting step includes applying the Kalman-Bucy filter according to the following formulas:

$$A_k = A_k^{(prior)} + \hat{K} \cdot \{\vec{H} - \hat{G} \cdot A_k^{(prior)}\}$$

$$\hat{M} = \hat{K} \cdot \{\hat{I} - \hat{K}\hat{G}\} \cdot \hat{M}^{(prior)}$$

Here, $A_k$ corresponds to the estimated Zernike amplitude profile for the patient eye, $A_k^{(prior)}$ corresponds to the a priori mean Zernike amplitude profile associated with the multiple general population corneal surfaces, $\hat{K}$ represents a Kalman-Bucy gain, H corresponds to a vector of the measured elevation field for the patient eye corneal surface, and $\hat{G}$ is an operator of surface reconstruction from the Zernike amplitudes. Further, $\hat{M}$ corresponds to the estimated Zernike amplitude covariance matrix for the patient eye, $\hat{I}$ is a unitary matrix, and $\hat{M}^{(prior)}$ corresponds to the a priori covariance Zernike amplitude profile associated with the multiple general population corneal surfaces.

In another aspect, embodiments of the present invention encompass systems and methods for planning a refractive correction treatment for an eye of a patient. Exemplary methods include obtaining a measured Zernike amplitude profile for the patient eye, where the measured Zernike amplitude profile is based on a measured elevation field for a corneal surface of the patient eye, and combining the measured Zernike amplitude profile with a priori corneal surface information to provide an estimated Zernike amplitude profile and an estimated Zernike amplitude covariance matrix for the patient eye. In some instances, the a priori corneal surface information includes mean and covariance Zernike amplitude profiles associated with multiple corneal surfaces of a general population. Further, methods may include constructing a corneal topography uncertainty map for the patient based on the estimated Zernike covariance matrix, constructing a corneal topography map for the patient based on the estimated Zernike amplitude profile and the corneal topography uncertainty map, and determining ablation properties locally across the corneal surface of the patient eye based on the corneal topography map. Further, methods may include formulating a treatment plan using the ablation properties by adjusting a first virtual ablation shape to form a second virtual ablation shape, where the first virtual shape represents a depth of material to be removed from a treatment area to form a desired shape, and where the second virtual shape is formed from the first virtual shape in response to the corneal topography map.

In another aspect, embodiments of the present invention encompass systems and methods for treating a cornea of a patient eye with a laser beam. Exemplary methods include obtaining a measured Zernike amplitude profile for the patient eye, where the measured Zernike amplitude profile based on a measured elevation field for a corneal surface of the patient eye, and combining the measured Zernike amplitude profile with a priori corneal surface information to provide an estimated Zernike amplitude profile and an estimated Zernike amplitude covariance matrix for the patient eye. In some instances, the a priori corneal surface information can include mean and covariance Zernike amplitude profiles associated with multiple corneal surfaces of a general population. Further, methods may include constructing a corneal topography uncertainty map for the patient based on the estimated Zernike covariance matrix, constructing a corneal topography map for the patient based on the estimated Zernike amplitude profile and the corneal topography uncertainty map, mapping angles between the corneal surface and the laser beam over a treatment area, determining ablation properties locally across the treatment area in response to the mapped angles, and formulating a treatment plan using the ablation properties by adjusting a first virtual ablation shape to form a second virtual ablation shape, where the first virtual shape represents a depth of material to be removed from the treatment area to form a desired shape, and the second virtual shape is formed from the first virtual shape in response to the mapped angles. Methods may also include ablating the treatment area according to the treatment plan to form the desired shape in the corneal surface. In some instances, the desired shape is based at least in part on a result of a measurement such as an aberration measurement of the eye, a refractive measurement of the eye, or a topography measurement of the eye.

In another aspect, embodiment of the present invention encompass systems and methods for treating a corneal surface of a patient eye with a laser beam, where the eye has a refractive defect, and where a desired refractive correcting shape mitigates the refractive defect. Exemplary systems include a laser emitting a beam of an ablative light energy, and at least one processor coupled to the laser beam and having a computer program, where the computer program embodies instructions for combining a measured Zernike amplitude profile for the patient eye with a priori corneal surface information to provide an estimated Zernike amplitude profile and an estimated Zernike amplitude covariance matrix for the patient eye. In some cases, the a priori corneal surface information comprising mean and covariance Zernike amplitude profiles associated with multiple corneal surfaces of a general population. The computer program can also embody instructions for constructing a corneal topography uncertainty map for the patient based on the estimated Zernike covariance matrix, constructing a corneal topography map for the patient based on the estimated Zernike amplitude profile and the corneal topography uncertainty map, determining ablation properties locally across the corneal surface of the patient eye based on the corneal topography map, and formulating a treatment plan using the ablation properties by adjusting a first virtual ablation shape to form a second virtual ablation shape, where the first virtual shape represents a depth of material to be removed from a treatment area to form a desired shape, and the second virtual shape is formed from the first virtual shape in response to the corneal topography map. Further, the computer program can embody instructions for controlling an ablative treatment using the treatment plan from the second virtual shape so that the treatment forms the desired refractive correcting shape in the surface.

In yet another aspect, embodiments of the present invention encompass systems and methods for evaluating an optical tissue of an eye. Exemplary methods include combining a measured orthogonal polynomial amplitude profile for the patient eye with a priori optical tissue information to provide an estimated orthogonal polynomial amplitude profile and an estimated orthogonal polynomial amplitude covariance matrix for the patient eye. In some cases, the a priori optical tissue information includes mean and covariance orthogonal polynomial amplitude profiles associated with multiple optical tissue measurements of a general population. Further, methods may include constructing an optical tissue uncertainty map for the patient based on the estimated orthogonal polynomial covariance matrix, where the uncertainty map represents a measure of measurement quality. Methods may also include evaluating the optical tissue of the patient eye based on the estimated orthogonal polynomial amplitude profile and the optical tissue uncertainty map. In some cases, the measured orthogonal polynomial amplitude profile for the patient eye is based on a measurement such as a corneal surface topography measurement of the eye or a wavefront measurement of the eye.

In still another aspect, embodiments of the present invention encompass systems and methods for evaluating the accuracy of an optical tissue measurement of an eye of a patient. Exemplary methods include obtaining amplitude data corresponding to the optical tissue measurement of the patient eye, obtaining amplitude data and covariance data corresponding to optical tissue measurements of multiple eyes of a population, and combining the amplitude data corresponding to the patient measurement with the amplitude data and covariance data corresponding to the population measurements, so as to obtain estimated amplitude data and estimated covariance data. Further, methods may include constructing a representation of the patient optical tissue based on the estimated amplitude data, constructing an uncertainty representation of the patient optical tissue based on the estimated covariance data, and evaluating the accuracy of the optical tissue measurement based on the representation of the patient optical tissue and the uncertainty representation of the patient optical tissue.

In another aspect, embodiments of the present invention encompass systems and methods for measuring a topography of a corneal surface. Exemplary methods may include measuring a plurality of elevations for a corneal surface, combining the measured elevations with a priori information of the corneal surface to provide an estimate of mean and covariance of post-measurement Zernike amplitudes associated with the corneal surface. The a priori information may include a plurality of mean and covariance of pre-measurement Zernike amplitudes associated with the corneal surface known prior to the measuring step. Methods may also include determining a variance of elevation of the corneal surface from the estimate, and constructing the topography of the corneal surface from the estimate based on a comparison of the variance with a pre-determined threshold. In some cases, methods may include estimating the plurality of mean and covariance of Zernike amplitudes associated with the corneal surface prior to the measuring step. In some cases, methods may include decomposing each of the measured elevations into a Zernike series representation. In some cases, methods may include acquiring topography elevation fields measured of human eyes, decomposing each of the topography elevation fields into a Zernike series, evaluating a mean and a variance of each amplitude of the Zernike series, and preparing the a priori information from the mean and the variance of each amplitude of the Zernike series. In some methods, the combining step includes inputting the a priori information into a Kalman-Bucy filter together with the measured elevations. In some methods, the inputting step includes applying the Kalman-Bucy filter according to the following formulas:

$$A_k^+ = A_k^- + \hat{K} \cdot \{H - \hat{G} \cdot A_k^-\}, \; M_k^+ = \hat{K} \cdot \{\hat{I} - \hat{K}\hat{G}\} \cdot M_k^-$$

$$\hat{K} = \hat{M}^{-1} \hat{G}^T \hat{F}$$

$$\hat{F} = \{\hat{G} M^- \hat{G}^T + \hat{N}\}^{-1}$$

where $A_k^-$ represents Zernike amplitudes prior to assimilation of measurement data, $M_k^-$ is a covariance matrix of $A_k^-$, $A_k^+$ represents Zernike amplitudes after assimilation of measurement data, $M_k^+$ is a covariance matrix of $A_k^+$, H is a vector of the measured elevations, $\hat{G}$ is an operator of surface reconstruction from the Zernike amplitudes, $\hat{K}$ is a Kalman-Bucy gain, $\hat{F}$ is a D×D matrix, $\hat{N}$ is a data noise covariance matrix, $\hat{M}$ is covariance matrix of the measured amplitudes, and $\hat{I}$ is a unitary matrix.

In another aspect, embodiments of the present invention encompass systems and methods for planning a refractive correction treatment for an eye. Exemplary methods may include measuring a plurality of elevations for a corneal surface of the eye, and combining the measured elevations with a priori information of the corneal surface to provide an estimate of mean and covariance of post-measurement Zernike amplitudes associated with the corneal surface. The a priori information may include a plurality of mean and covariance of pre-measurement Zernike amplitudes associated with the corneal surface known prior to the measuring step. Further, methods may include determining a variance of elevation of the corneal surface from the estimate, constructing the topography of the corneal surface from the estimate based on a comparison of the variance with a pre-determined threshold, determining ablation properties locally across the corneal surface based on the topography, and formulating a treatment plan using the ablation properties by adjusting a first virtual ablation shape to form a second virtual ablation shape. In some cases, the first virtual shape represents a depth of material to be removed from the treatment area to form a desired shape, and the second virtual shape is formed from the first virtual shape in response to the topography.

In another aspect, embodiments of the present invention encompass systems and methods for treating a cornea of a patient's eye with a laser beam. Exemplary methods may include measuring a plurality of elevations for a surface of the cornea, and combining the measured elevations with a priori information of the surface to provide an estimate of mean and covariance of post-measurement Zernike amplitudes associated with the surface. In some cases, the a priori information includes a plurality of mean and covariance of pre-measurement Zernike amplitudes associated with the surface known prior to the measuring step. Further, methods may include determining a variance of elevation of the corneal surface from the estimate, constructing the topography of the corneal surface from the estimate based on a comparison of the variance with a pre-determined threshold, mapping angles between the surface and the laser beam over a treatment area, determining ablation properties locally across the treatment area in response to the mapped angles, and formulating a treatment plan using the ablation properties by adjusting a first virtual ablation shape to form a second virtual ablation shape. In some cases, the first virtual shape represents a depth of material to be removed from the treatment area to form a desired shape, and the second virtual shape is formed from the first virtual shape in response to the mapped angles. What is more, methods may include ablating the treatment area according to the treatment plan to form the desired shape in the surface. In some cases, the desired shape is based at least in part on a result of a measurement such as an aberration measurement of the eye, a refractive measurement of the eye, or a topography measurement of the eye.

In another aspect, embodiments of the present invention encompass systems and methods for treating a corneal surface of a patient's eye with a laser beam, where the eye has a refractive defect, and where a desired refractive correcting shape mitigates the refractive defect. Exemplary systems may include a laser emitting a beam of an ablative light energy, and at least one processor coupled to the laser beam and having a computer program. The computer program may embody instructions for combining measured elevations of the corneal surface with a priori information of the corneal surface to provide an estimate of mean and covariance of post-measurement Zernike amplitudes associated with the corneal surface. In some cases, the a priori information may include a plurality of mean and covariance of pre-measurement Zernike amplitudes associated with the corneal surface known prior to the measuring step. The computer program may further embody instructions for determining a variance of elevation of the corneal surface from the estimate, constructing the topography of the corneal surface from the estimate based on a comparison of the variance with a pre-determined threshold, determining ablation properties locally across the corneal surface based on the topography, and formulating a treatment plan using the ablation properties by adjusting a first virtual ablation shape to form a second virtual ablation shape. The first virtual shape may represent a depth of material to be removed from the treatment area to form a desired shape, the second virtual shape may be formed from the first virtual shape in response to the topography. What is more, the computer program may embody instructions for controlling an ablative treatment using the treatment plan from the second virtual shape so that the treatment forms the desired refractive correcting shape in the surface.

In some aspects, embodiments of the present invention encompass systems and methods for measuring a topography of an optical tissue surface of an eye. Exemplary methods may include combining measured elevations of the surface with a priori information of the surface to provide an estimate of mean and covariance of post-measurement orthogonal polynomial sequence amplitudes associated with the surface. In some cases, the a priori information includes an estimate of mean and covariance of pre-measurement orthogonal polynomial sequence amplitudes associated with the surface. Methods may also include determining a variance of elevation of the surface from the estimate of mean and covariance of post-measurement amplitudes associated with the surface, where the variance represents a measure of measurement quality. Methods may also include constructing the topography from the estimate of mean and covariance of post-measurement amplitudes based on a comparison of the variance of elevation of the surface with a pre-determined threshold. In some cases, the optical tissue surface can be a corneal surface of the eye or a wavefront of the eye.

Embodiments of the present invention provide ophthalmic treatment and diagnostic techniques based on measurement data assimilation of corneal topography and/or wavefront measurements. In one particular embodiment, the data assimilation technique is based on a Kalman-Bucy technique to combine measured corneal elevations with a priori information, including mean and covariance of Zernike amplitudes for a measured surface known prior to the measurement. This technique provides a statistically optimal estimate of post-measurement mean and covariance of Zernike amplitudes. A priori mean and covariance before any measurements can be estimated from an ensemble of available data. Repeated measurements of the same eye can use mean and covariance from the preceeding measurement in combination with the current measurement. In some embodiments of the present invention, systems and methods are provided for treating a tissue of an eye with a laser beam based on an ablation pattern or refractive correction determined from the corneal topography and wavefront measurements assimilated in accordance with the foregoing technique. In some embodiments of the present invention, systems and methods are provided for determining refractive corrections of an eye from corneal topography and wavefront measurements assimilated in accordance with the foregoing technique.

In one aspect, the invention comprises a method of treating a cornea of a patient's eye with a laser beam. Angles between a surface of a cornea and a laser beam are mapped over a treatment area. Ablation properties are determined locally across a treatment area in response to mapped angles so as to formulate a treatment plan using local ablation properties. A treatment area is ablated according to the treatment plan to form a desired shape in a surface.

In some embodiments, an angle of a laser beam may be substantially parallel to an optical axis of an eye. A mapped area includes an apex of a cornea and an apex of a cornea is displaced from a center of a pupil of an eye. A desired shape has a center, and a center of a desired shape may be aligned with a center of a pupil of an eye. A virtual shape may be adjusted from a first virtual shape to a second virtual shape. A first virtual shape may represent a depth of material removed from an area to form a desired shape. A second virtual shape may be formed from a first virtual shape in response to the mapped angles. In an embodiment, a depth of a second virtual shape may be greater than a depth of a first virtual shape. In another embodiment, a depth of a second virtual shape may be less than a depth of a first virtual shape. A desired shape may be based at least in part on a result of measurement selected from a group consisting of an aberration measurement of an eye, a refractive measurement of an eye, and a topography measurement of an eye.

In another aspect, embodiments of the invention comprise a system for treating a cornea of a patient's eye with a laser beam. The system includes a laser emitting a beam of an ablative light energy and at least one processor. At least one processor has a computer program mapping angles between a surface of a cornea and a laser beam. At least one processor determines local ablation properties of a cornea in response to mapped angles. At least one processor has a computer program controlling an ablative treatment in response to local ablation properties. A treatment forms a desired shape in a surface.

In some embodiments, an angle of a laser beam may be substantially parallel to an optical axis of an eye. A mapped area may include an apex of a cornea, and an apex of a cornea may be displaced from a center of a pupil of an eye. A desired shape may have a center, and a center of a desired shape may be aligned with a center of a pupil of an eye. At least one processor having a computer program may include a first virtual shape and a second virtual shape. A first virtual shape may represent a depth of material removed from an area to form a desired shape, and a second virtual shape may be formed from a first virtual shape in response to mapped angles. In an embodiment, a depth of a second virtual shape may be greater than a depth of a first virtual shape. In another embodiment, a depth of a second virtual shape may be less than a depth of a first virtual shape. A desired shape may be based at least in part on a result of measurement selected from a group consisting of an aberration measurement of an eye, a refractive measurement of the eye, and a topography measurement of the eye.

In a further aspect, the invention comprises a system for treating a cornea of an eye with a laser beam. A system includes a laser emitting a beam of an ablative light energy and at least one processor having a computer program. At least one processor determines angles between a curved surface and a laser beam. At least one processor has a computer program controlling an ablative treatment in response to angles between a curved surface and a laser beam. A treatment forms a desired shape in a surface.

In specific embodiments, at least one processor determines local ablation properties of a cornea in response to angles between a curved surface and a laser beam. An angle of a laser beam is substantially parallel to an optical axis of an eye. A mapped area includes an apex of a cornea and an apex of a cornea is displaced from a center of a pupil of an eye. A desired shape has a center, and a center of a desired shape is aligned with a center of a pupil of an eye. At least one processor has a computer program including a first virtual shape and a second virtual shape. A first virtual shape represents a depth of material removed from an area to form a desired shape. A second virtual shape is formed from a first virtual shape in response to mapped angles. In an embodiment, a depth of a second virtual shape is greater than a depth of a first virtual shape. In another embodiment, a depth of a second virtual shape is less than a depth of a first virtual shape. A desired shape is based at least in part on a result of a measurement selected from a group consisting of an aberration measurement of an eye, a refractive measurement of the eye, and a topography measurement of an eye.

For a fuller understanding of the nature and advantages of the present invention, reference should be had to the ensuing detailed description taken in conjunction with the accompanying drawings.

DETAILED DESCRIPTION OF THE INVENTION

Figure 1:
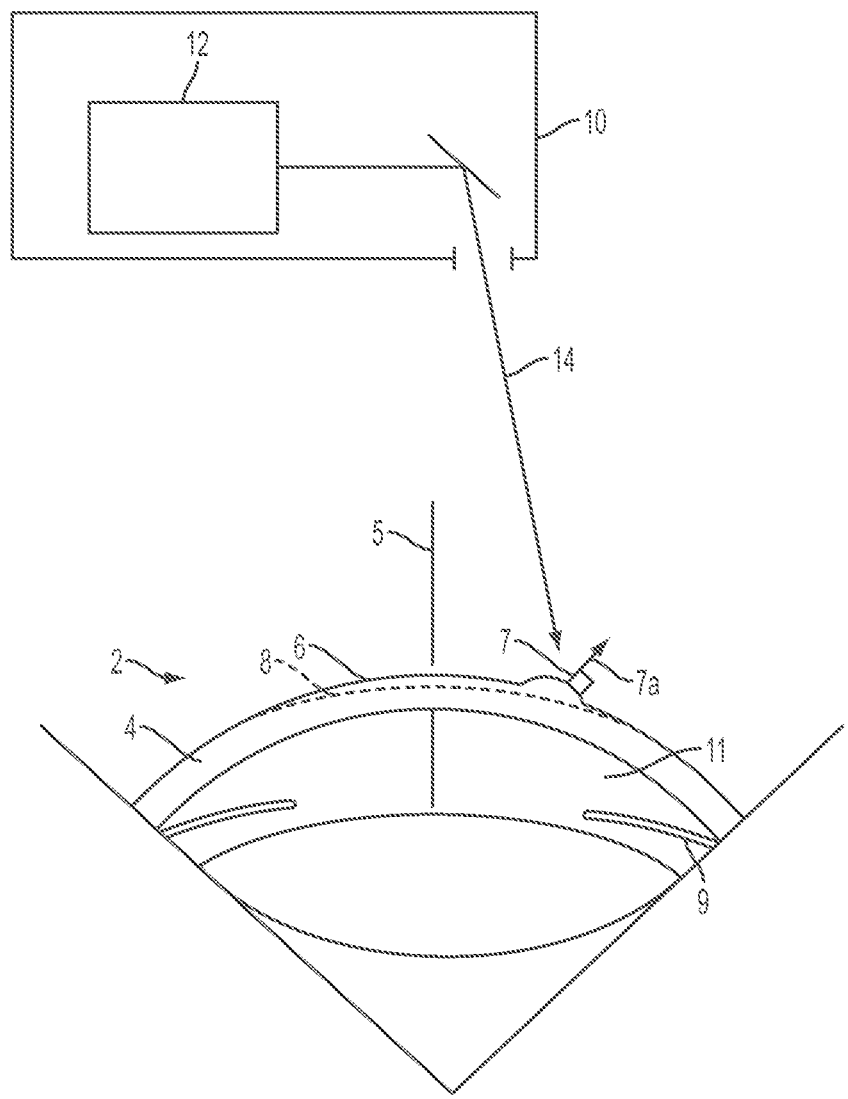
FIG. 1 illustrates a laser system ablating a tissue surface in accord with an embodiment of the present invention.

Embodiments of the present invention are particularly useful for enhancing the accuracy and efficacy of laser eye surgical procedures, such as photorefractive keratectomy (PRK), phototherapeutic keratectomy (PTK), laser assisted in situ keratomileusis (LASIK), laser epithelial keratomileusis (LASEK) and the like. In some instances, embodiments of the present invention can provide enhanced optical accuracy of refractive procedures by improving a corneal ablation of a refractive treatment program. Hence, while certain system and method embodiments of the present invention are described primarily in a context of a laser eye surgery system, it should be understood that techniques of the present invention may be adapted for use in alternative eye treatment procedures and systems such as spectacle lenses, intraocular lenses, contact lenses, corneal ring implants, collagenous corneal tissue thermal remodeling, and the like. Certain techniques of embodiments of the present invention can be readily adapted for use with existing laser systems, wavefront sensors, corneal topography systems, phoropters and other optical measurement devices as well as treatment planning regimes. By providing a methodology for determining a laser treatment plan that more accurately reflects various characteristics of one or more optical tissue surfaces of the eye, embodiments of the present invention may facilitate sculpting of the cornea so that treated eyes more accurately result in a desired visual correction.

As used herein an "optical tissue surface" may encompass a theoretical tissue surface derived from an optical measurement of light refraction of an eye (exemplified by wavefront sensor data and manifest refraction data), an actual tissue surface, and/or a tissue surface formed for purposes of treatment (for example, by incising corneal tissues so as to allow a flap of the corneal epithelium to be displaced and expose the underlying stroma during a LASIK procedure).

Systems and methods for measuring a refractive error of an eye such as spherical defocus and cylindrical astigmatism having an axis are well known in the optometric and ophthalmic fields. Examples of measurements of a refractive error of an eye are manifest, cycloplegic, and retinoscopic refraction. U.S. Pat. No. 5,163,934, the full disclosure of which is incorporated herein by reference, describes a shape of tissue to be removed from a cornea of an eye to correct a refractive error of an eye. Systems and methods for measuring a corneal topography of an eye are well known in the optometric and ophthalmic fields. For example, U.S. Pat. Nos. 4,761,071, 4,995,716, 5,406,342, 6,396,069, 6,116,738, 4,540,254 and 5,491,524, the full disclosures of which are incorporated herein by reference, describe systems and methods for measuring a corneal topography of an eye. Systems and methods for determining an ablation location and shape using corneal topography are described in U.S. Pat. Nos. 6,245,059, 6,129,722 and 5,843,070, the full disclosures of which are incorporated herein by reference.

Wavefront sensors will typically measure aberrations and other optical characteristics of an entire optical tissue system. Data from such a wavefront sensor may be used to generate an optical tissue surface from an array of optical gradients. In some instances, an optical tissue surface may be referred to as a wavefront elevation map. An optical tissue surface may not precisely match an actual tissue surface. For example, optical gradients will show effects of aberrations, which are actually located throughout an ocular tissue system. Nonetheless, corrections imposed on an optical tissue surface so as to correct aberrations derived from gradients should correct an optical tissue system. Systems and methods for measuring and correcting aberrations of an optical tissue surface of eye based on wavefront elevation maps are described in U.S. Pat. Nos. 5,777,719, 6,042,012, 6,095,651, 6,199,986, 6,271,914 and 6,217,915, the full disclosures of which are incorporated herein by reference.

In correcting an optical tissue surface of an eye, a shape of tissue to be removed is typically determined prior to ablation. A predetermined shape is often the result of a combination of refractive error, wavefront sensor and topography measurements as described above.

A laser ablating a surface of an eye is illustrated in FIG. 1 in accordance with an embodiment of the invention. An eye 2 is illustrated in cross section as being ablated by a laser system 10 having a laser 12 emitting a beam 14 of an ablative light energy. The eye 2 has a cornea 4 and a pupil 11 formed in an iris 9. The cornea 4 has a surface 6 and a local surface angle 7 associated therewith. In some embodiments, the local surface angle 7 is a surface normal vector 7a, but can be any representation of a local slope of surface 6. The eye 2 has at least one axis, for example an optical axis 5, and the optical axis 5 is preferably aligned with the laser system 10. A desired predetermined shape 8 is formed in the surface 6 with a series of pulses of the laser beam 14 of ablative light energy.

As tissue ablates from surface 6 to form the predetermined shape 8, an amount of tissue ablated with each pulse of laser beam 14 varies with an angle between the surface angle 7 and the laser beam 14. Typically, an amount of tissue removed with each pulse of the laser beam 14 will decrease as the local surface having the angle 7 faces away from the laser beam 14. By determining a local amount of ablation from a local angle between a local surface angle and a local angle of laser beam incident on the local surface, a treatment program will more accurately calculate a distribution pattern of a series of pulses to form the desired predetermined shape 8.

Figure 1A:
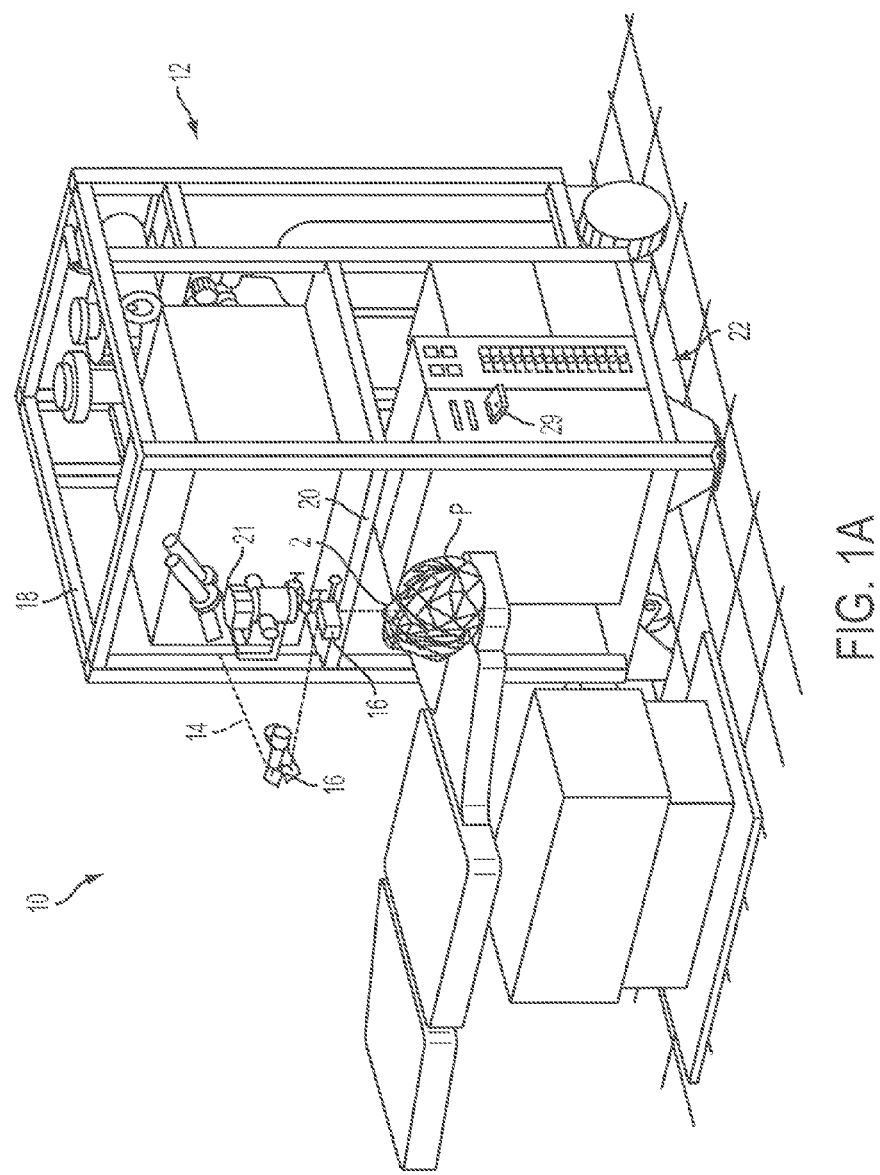
FIG. 1A is a perspective view of a laser ablation system for incorporating embodiments of the present invention.

Referring now to FIG. 1A, a laser eye surgery system 10 for incorporating the present invention includes the laser 12 that produces a laser beam 14. Laser delivery optics 16 are in a path of laser beam 14, and the delivery optics 16 direct the laser beam 14 to an eye of a patient P. A delivery optics support structure (not shown here for clarity) extends from a frame 18 supporting the laser 12. An input device 20 is used to align laser system 10 in relation to an eye of a patient P. A microscope 21 is mounted on the delivery optics support structure, the microscope often being used to image a cornea of an eye. In various embodiments, a laser eye surgery system 10 includes at least some portions of a STAR S4 IR® Excimer Laser System available from Abbott Medical Optics Inc.

While the input device 20 is schematically illustrated as a joystick, a variety of input components may be used. Suitable input components may include trackballs, touch screens, or a wide variety of alternative pointing devices. Still further alternative input components include keypads, data transmission mechanisms such as an Ethernet, intranet, Internet, a modem, or the like.

The laser 12 generally comprises an excimer laser, such as an argon-fluoride laser producing pulses of laser light having a wavelength of approximately 193 nm. The pulse of laser light typically has a fixed pulse duration having a full width half maximum (FWHM) of about 15 nanoseconds during a treatment. The laser 12 is preferably designed to provide a feedback stabilized fluence at the patient's eye, delivered via the delivery optics 16. The present invention may also be useful with alternative sources of ultraviolet or infrared radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193-215 nm) such as those described in U.S. Pat. Nos. 5,144,630 and 5,742,626, Borsurtky et al., "Tunable UV Radiation at Short Wavelengths (188-240 nm) Generated by Sum Frequency Mixing in Lithium Borate", Appl. Phys. 61:529-532 (1995), and the like. Laser energy may comprise a beam formed as a series of discreet laser pulses. A variety of alternative lasers might also be used. Hence, although an excimer laser is the illustrative source of an ablating beam, other lasers may be used in the present invention.

The laser 12 and delivery optics 16 generally direct the laser beam 14 to an eye of patient P under direction of a processor 22. The processor 22 often selectively adjusts the laser beam 14 to expose portions of the cornea to pulses of laser energy so as to effect a predetermined sculpting of a cornea and alter refractive characteristics of an eye. In many embodiments, both the laser 14 and laser delivery opticals 16 are under computer control of the processor 22 to effect a desired laser sculpting process, with the processor 22 effecting (and optionally modifying) a pattern of laser pulses. A pattern of pulses may by summarized in a treatment table listing of machine readable data of a tangible storage media 29. The treatment table can be adjusted according to feedback input into the processor 22 from an automated image analysis system (e.g., manually input into processor 22 by a system operator) in response to feedback data provided from an ablation monitoring system feedback system. Such feedback might be provided by integrating a wavefront measurement system described below with the laser treatment system 10, and the processor 22 may continue and/or terminate a sculpting treatment in response to feedback, and may also optionally modify a planned sculpting based at least in part on feedback.

The laser beam 14 can be adjusted to produce a desired sculpting using a variety of alternative mechanisms and may be selectively limited using one or more variable apertures. An exemplary variable aperture system having a variable iris and a variable width slit is described in U.S. Pat. No. 5,713,892, the full disclosure of which is incorporated herein by reference. A laser beam may also be tailored by varying a size and offset of a laser spot from an axis of an eye, as described in U.S. Pat. No. 5,683,379, and as also described in co-pending U.S. patent application Ser. No. 08/968,380, filed Nov. 12, 1997; Ser. No. and 09/274,999 filed Mar. 22, 1999, the full disclosures of which are incorporated herein by reference.

Still further alternatives are possible, including scanning a laser beam over a surface of an eye and controlling a number of pulses and/or dwell time at each location, as described, for example, by U.S. Pat. No. 4,665,913 (the full disclosure of which is incorporated herein by reference); using masks in an optical path of the laser beam 14 which ablate to vary a profile of a beam incident on a cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea as described in U.S. Pat. Nos. 6,319,247; 6,280,435; and 6,203,539, the full disclosures of which are incorporated herein by reference; or the like. The computer programs and control methodology for these laser pattern tailoring techniques are well described in the patent literature.

Additional components and subsystems may be included with the laser system 10, as should be understood by those of skill in the art. For example, spatial and/or temporal integrators may be included to control the distribution of energy within the laser beam, as described in U.S. Pat. Nos. 5,646,791 and 5,912,779, the full disclosures of which are incorporated herein by reference. An ablation effluent evacuator/filter, and other ancillary components of the laser surgery system that are not necessary to an understanding of the invention, and which may be optionally employed, need not be described in detail for an understanding of the present invention.

The processor 22 comprises (or interfaces with) a conventional PC system including standard user interface devices such as a keyboard, a display monitor, and the like. The processor 22 typically includes an input device such as a magnetic or optical disk drive, an internet connection, or the like. Such input devices are often used to download a computer executable code from the storage media 29 embodying any methods of the present invention. The storage media 29 may comprise a floppy disk, an optical disk, a data tape, a volatile or non-volatile memory, or the like, and the processor 22 will include memory boards and other standard components of modern computer systems for storing and executing a computer program code. The storage media 29 may optionally embody wavefront sensor data, wavefront gradients, a wavefront elevation map, a treatment map, a corneal topography map, a measurement of a refraction of an eye, and an ablation table.

Figure 2:
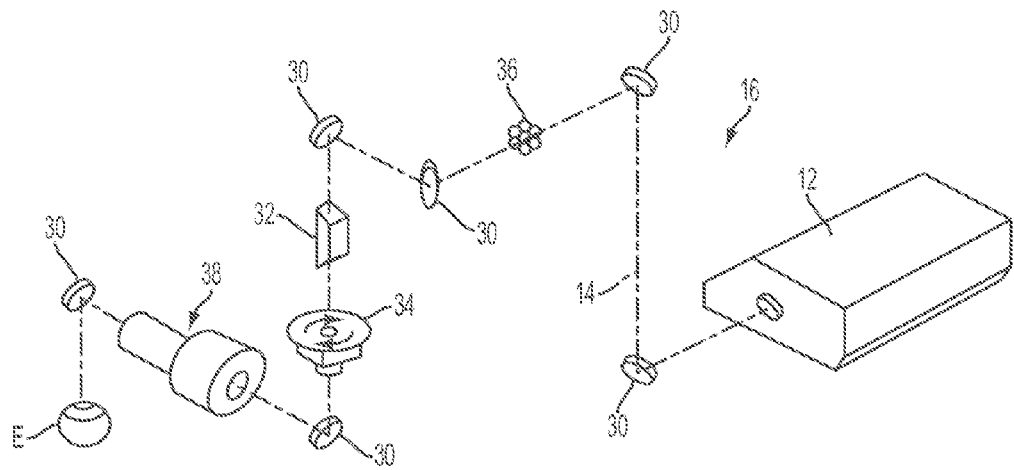
FIGS. 2 and 3 schematically illustrate a laser beam delivery system for selectively directing a laser beam onto a corneal tissue in accord with an embodiment of the present invention.

Referring now to FIG. 2, the laser beam delivery system 16 for directing the laser beam 14 at the eye 2 includes a number of mirrors 30, as well as one or more temporal integrators 32 that may adjust (or otherwise tailor) an energy distribution across a laser beam. The laser 12 often comprises an excimer laser as described above.

Figure 3:
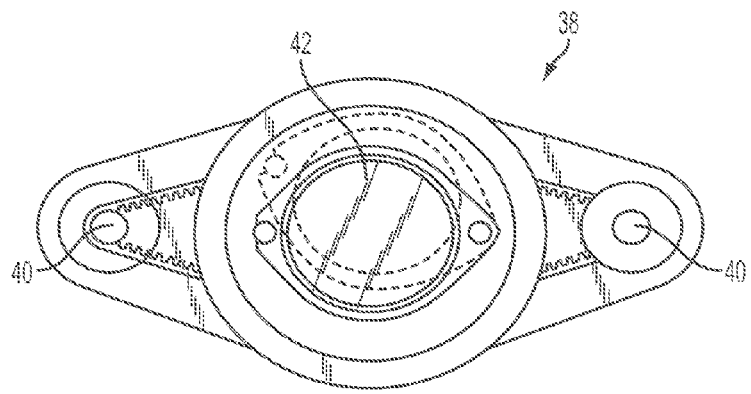

In an exemplary embodiment, a variable aperture 34 changes a diameter and/or slot width to profile laser beam 14, ideally including both a variable diameter iris and a variable width slot. A prism 36 separates the laser beam 14 into a plurality of beamlets, which may partially overlap on the eye 2 to smooth edges of an ablation or "crater" formed from each pulse of a laser beam. Referring now to FIGS. 2 and 3, an offset module 38 includes motors 40 which vary an angular offset of an offset lens 42, and which also change a radial orientation of an offset. Hence, the offset module 38 can selectively direct the laser beam 14 at a desired lateral region of a cornea. A structure and method for using embodiments of the laser beam delivery system 16 and the offset module 38 are more fully described in U.S. Pat. Nos.

6,331,177; 6,203,539; 5,912,775; and 5,646,791 the full disclosures of which are incorporated herein by reference.

Figure 4:
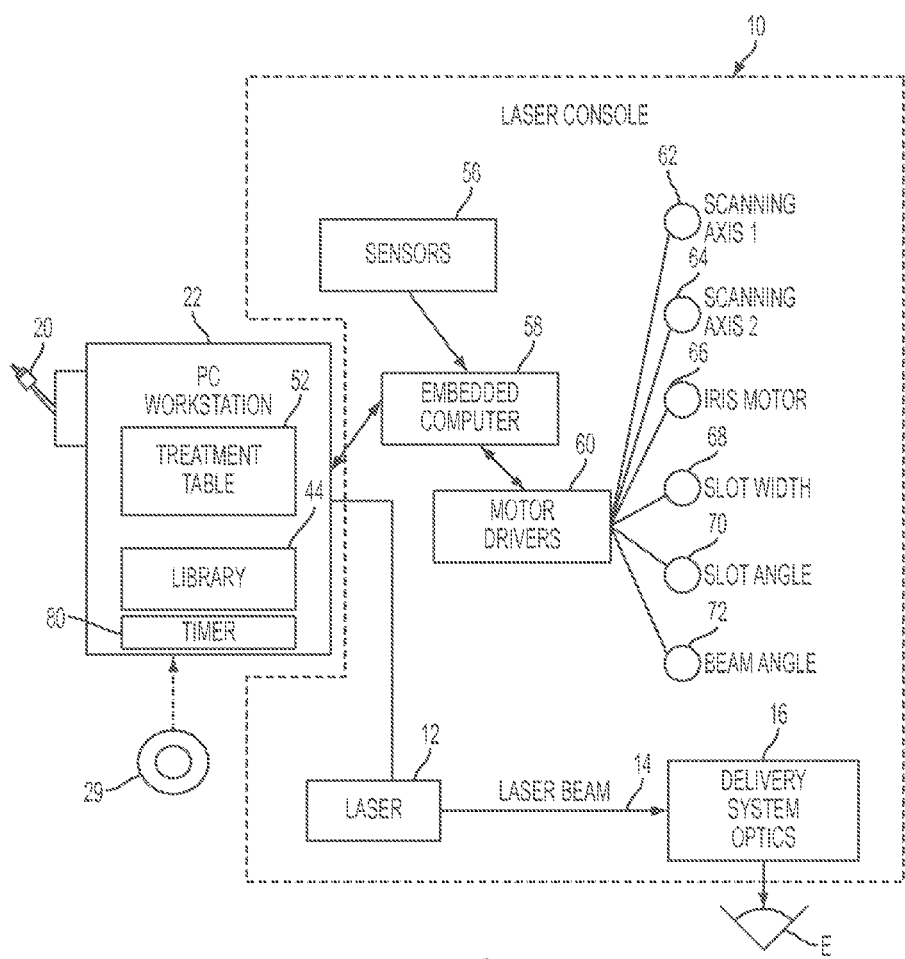
FIG. 4 is a functional block diagram illustrating a control architecture of an ablation system as in FIG. 1A in accord with an embodiment of the present invention.

Referring now to FIG. 4, a control system of the laser system 10 is schematically illustrated according to principles of the present invention. The processor 22 enables precise control of the laser system 10 to sculpt a surface shape according to a laser treatment table 52. The processor 22, generally comprising a PC workstation, makes use of a computer program stored on the tangible media 29 to generate the treatment table 52. The processor 22 includes a library 44 of treatments, such as described in U.S. Pat. No. 6,245,059, the full disclosure of which is incorporated herein by reference. An embedded computer 58 within the laser system 10 is in electronic communication with the PC workstation. Alternatively, a PC workstation may be embedded in the laser system 10 and include an embedded processor card in communication with a PC workstation for directing an ophthalmic surgery.

The embedded computer 58 is in electronic communication with a plurality of sensors 56 and a plurality of motor drivers 60. The motor drivers 60 are coupled to the embedded computer 58 to vary a position and configuration of many of the optical components of the delivery optics 16 according to the treatment table 52. For example, first and second scanning axes 62, 64 control a position of an offset lens to move several laser beamlets over a tissue surface of the cornea. An iris motor 66 controls an overall diameter of a beam, and in some cases, a length of light transmitted through a variable width slot. Similarly, a slot width driver 68 controls a width of a variable slot. A slot angle driver 70 controls rotation of a slot about its axis. A beam angle driver 72 controls beam rotation as effected by a temporal integrator as described above. A timer 80 controls a time interval between pulses of a laser treatment. The timer 80 measures a time interval from a previous pulse and generates an interrupt after a predetermined time interval has elapsed. The processor 22 issues a command for the laser 12 to generate a pulse of the laser beam 14 after various optical elements have been positioned to create a desired crater on the eye 2 and after a measured time interval has elapsed. The treatment table 52 comprises a listing of all desired craters to be combined so as to effect a treatment therapy.

Figure 5:
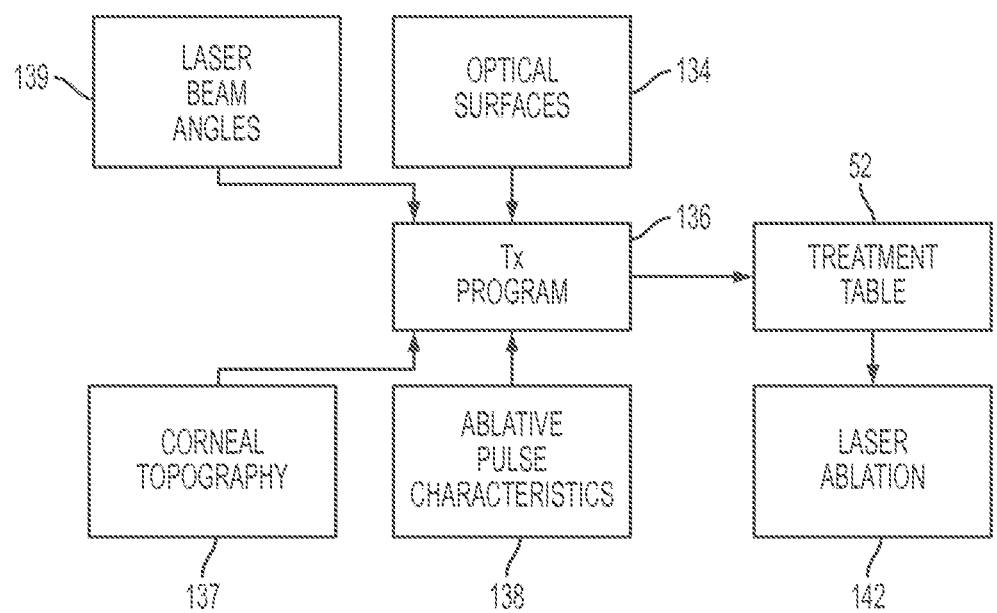
FIG. 5 is a flow chart schematically illustrating a method for determining a corneal ablation treatment program in accord with an embodiment of the present invention.

A flow chart schematically illustrating a method for determining a corneal ablation treatment plan is illustrated in FIG. 5 in accordance with an embodiment of the present invention. A treatment calculation program 136 uses properties of an optical tissue surface 134, corneal topography 137, ablative pulse characteristics 138, and laser beam angles 139 to determine a treatment plan listed in the treatment table 52. The optical tissue surface 134 includes information related to optical aberrations of the eye as described above. The corneal topography 137 includes a measured shape of at least one surface of the cornea, preferably a front or anterior surface as described above, and the corneal topography 137 preferably includes information locating a center of a pupil in relation to mapped corneal topography coordinates. The ablative pulse characteristics 138 include information describing a shape of tissue, or "crater" removed with a pulse of a laser beam. The local laser beam angles 139 include information describing several local angles of several rays for at least one laser beam incident on several locations of the cornea in relation to a reference axis, for example an optical axis of an eye as described above.

The treatment calculation program 136 combines information from the optical tissue surface 134 with corneal topography 137 to determine a desired shape of tissue to be removed from the surface 6 of the cornea 4 to form the desired shape 8 in the surface 6 in one embodiment. In another embodiment, a desired shape of tissue to be removed from the surface 6 may be calculated from an optical tissue surface, for example from a wavefront elevation map, without using corneal topography information. In another embodiment, the desired shape of tissue to be removed from the surface 6 may be calculated from the corneal topography information without using the wavefront information. The desired shape of tissue removed is preferably determined from a the optical tissue surface 134 so as to remove regular (spherical and/or cylindrical) and irregular errors of optical tissues as described above. Alternatively, the desired shape of tissue to be removed may be determined so as to modify the optical tissue surface 134 and leave controlled amounts of aberration, for example controlled amounts of aberrations correcting presbyopia or extending a depth of focus.

By combining in a treatment plan an optical tissue surface and the ablative laser pulse characteristics 138 of a particular laser system, the treatment table 52 of ablation pulse locations, sizes, shapes, and/or numbers can be developed. An exemplary method and system for preparing such an ablation table is described in U.S. Pat. Nos. 6,673,062 and 7,008,415, the full disclosures of which are incorporated herein by reference. Sorting of individual pulses to avoid localized heating, minimize irregular ablations if the treatment program is interrupted, and the like may optionally optimize the treatment table 52. Preferably, a series of pulses applied to an eye are listed in a treatment table and sorted to initially apply pulses having a small cross sectional dimension followed by pulses having a larger cross sectional dimension. Alternatively, a treatment table may be sorted to apply large diameter pulses to an eye initially followed by smaller diameter pulses, and an order of pulses may provide pulses having a random size distribution. An eye can then be treated by laser ablation 142 according to the treatment table 52.

Figure 6:
FIG. 6 illustrates a laser treatment table in accord with an embodiment the present invention.

Referring now to FIG. 6, several listings from an exemplary laser treatment table 140 are illustrated. A Patient Name 150, patient identification number (Patient ID) 154, and treated Eye 156 are listed in a treatment table 140. A repetition rate (reprate) 152 is also listed. A refraction 158 having a sphere of −3 D, a cylinder of −2.25D, an axis of 60 degrees and a vertex distance of 0 mm is listed in FIG. 6. A pulse count 160 as listed in FIG. 6 illustrates a total number of 1079 pulses applied to an eye during a treatment. Additional fields of the treatment table 140 are pulse number 170, iris diameter 172, slit width 174, slit axis 176, X coordinate 178, and Y coordinate 180.

For each pulse of the treatment table 140, a pulse number 170, iris diameter 172, slit width 174, slit axis 176, X coordinate 178 and Y coordinate 180 are listed. The X coordinate 178 and Y coordinate 180 list X and Y coordinates of a center of each pulse on a cornea relative to a treatment center during a treatment. An iris diameter field 172 lists a dimension across a circular iris diaphragm opening as projected onto an eye in millimeters for each pulse during treatment as described above. A slit width field 174 and a slit axis field 176 list a dimension across and an angle of a variable width slot opening as projected onto an eye as described above. A laser treatment table for scanning a variable width slot is described in U.S. Pat. No. 6,203,539, the full disclosure of which is incorporated herein by reference.

Figure 7:
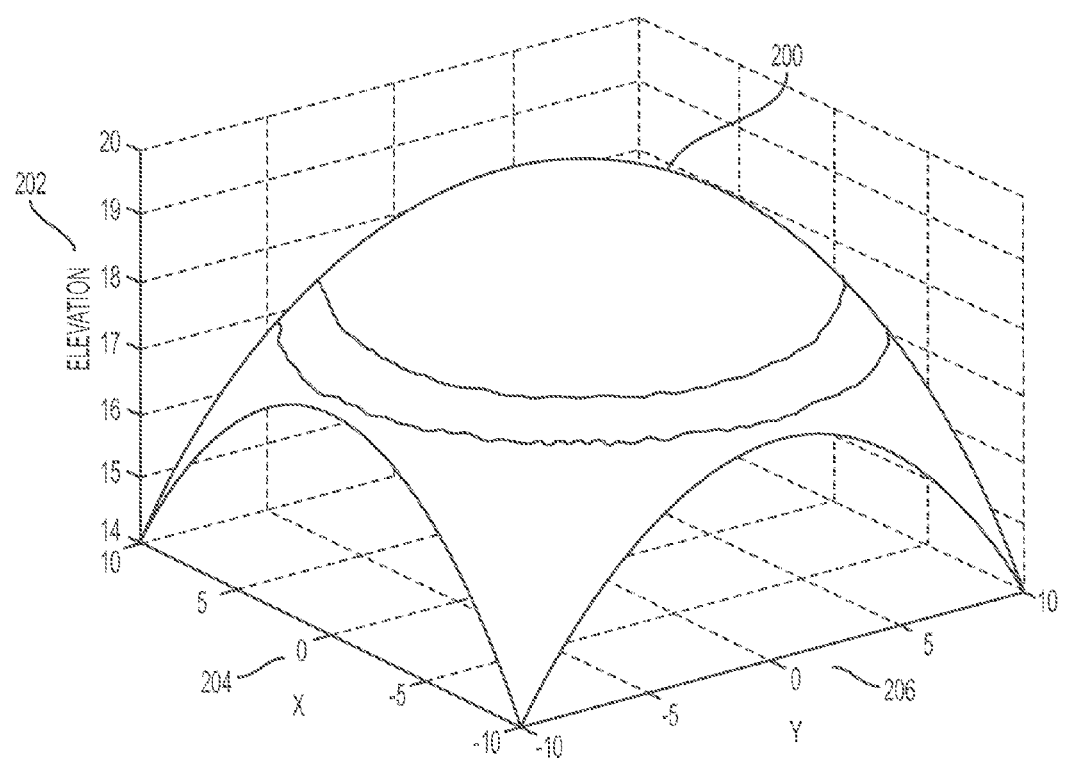
FIG. 7 illustrates a surface topography of a cornea in accord with an embodiment of the present invention.
Figure 8:
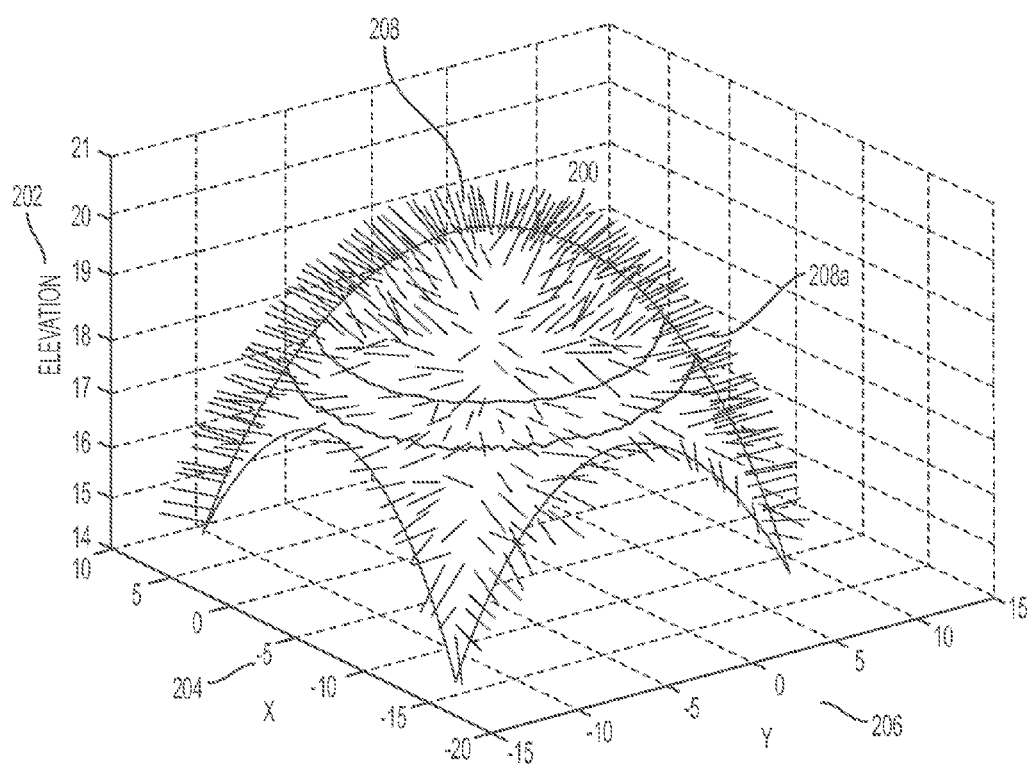
FIG. 8 illustrates local surface angles of a corneal surface topography as in FIG. 7 as surface normal vectors in accord with an embodiment of the present invention.

A map 200 of corneal surface elevation is illustrated in FIG. 7. The map 200 has an elevation 202 along a first dimension X 204 and a second dimension Y 206. For the map 200 of corneal surface elevation, several local surface angles are determined over a map 200 of a corneal surface as shown in FIG. 8. Several local surface angles are represented as several local surface normal vectors 208. An individual surface normal vector 208a is illustrated. The map 200 of corneal surface elevation 202 is expressed as a function Z(x,y) of the first dimension X 204 and the second dimension Y 206. Based on an elevation map, a surface normal vector 210 can be computed from Z(x,y) as:

$$N(x,y)=(Z_u \times Z_v)$$

where $Z_u$ and $Z_v$ are partial derivatives of the surface at point Z(x,y). A surface normal vector is preferably normalized to have a magnitude of 1. A normalized surface normal vector is expressed as $n(x,y)=N(x,y)/\|N\|$.

Figure 8A:
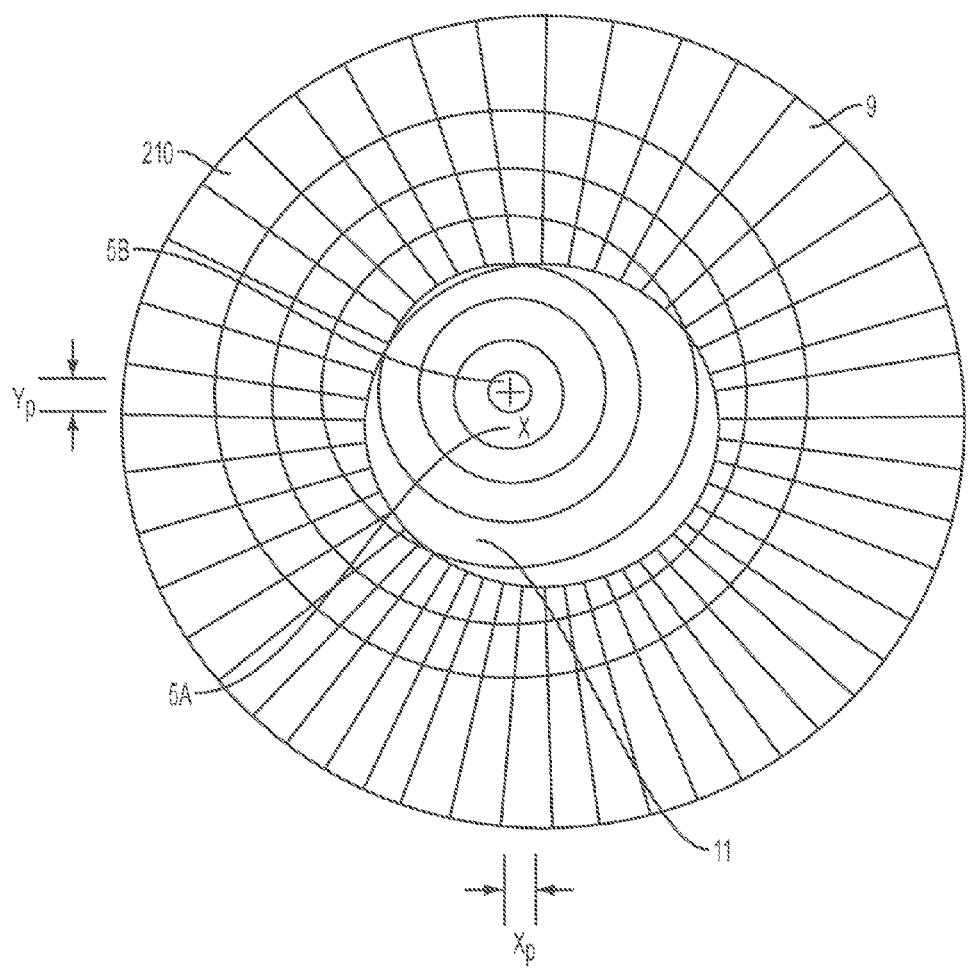
FIG. 8A illustrates a center of a pupil of an eye in relation to a center of a corneal topography measurement in accord with an embodiment of the present invention.

A measurement of a corneal topography of an eye and a pupil of an eye are illustrated in FIG. 8A. The pupil 11 is formed in the iris 9. Several rings 210 of light are reflected from a surface of a cornea during a topography measurement of the cornea. In this embodiment, a center of a topography measurement is near an apex of a cornea 5B. A center of a pupil 5A is illustrated as displaced from an apex of the cornea 5B. A center of a topography measurement is displaced from a center of a pupil by distances $X_p$ and $Y_p$ along first and second dimensions X and Y, respectively. Several commercially available corneal topography systems measure a corneal topography of an eye and a center of a pupil of an eye. For example, a Humphrey® Atlas™ Corneal Topography System is available from ZEISS HUMPHREY SYSTEMS.

Figure 8B:
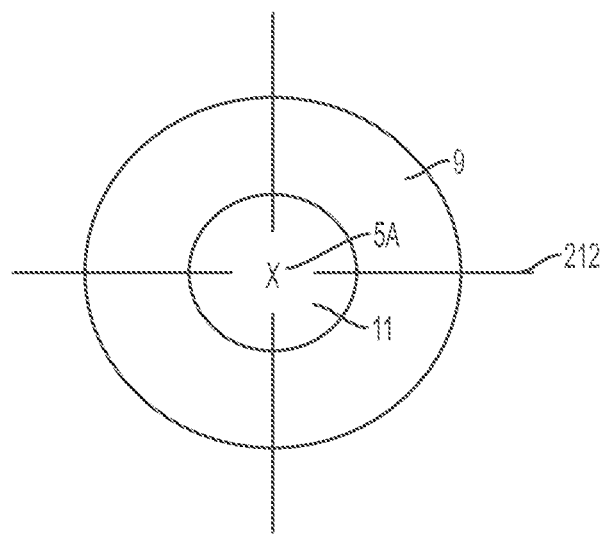
FIG. 8B illustrates a laser surgery system aligned with a center of an eye in accord with an embodiment of the present invention.

An alignment of an eye with the laser system 10 as described above is illustrated in FIG. 8B. The pupil 11 is formed in the iris 9. A reticule 212 is aligned with the center 5A of the pupil 11. In some embodiments, the system 10 may be aligned with any center of an eye, for example a center of a reflected image, such as a first Purkinje image, a center of a dilated pupil, and a center of a limbus.

Figure 9:
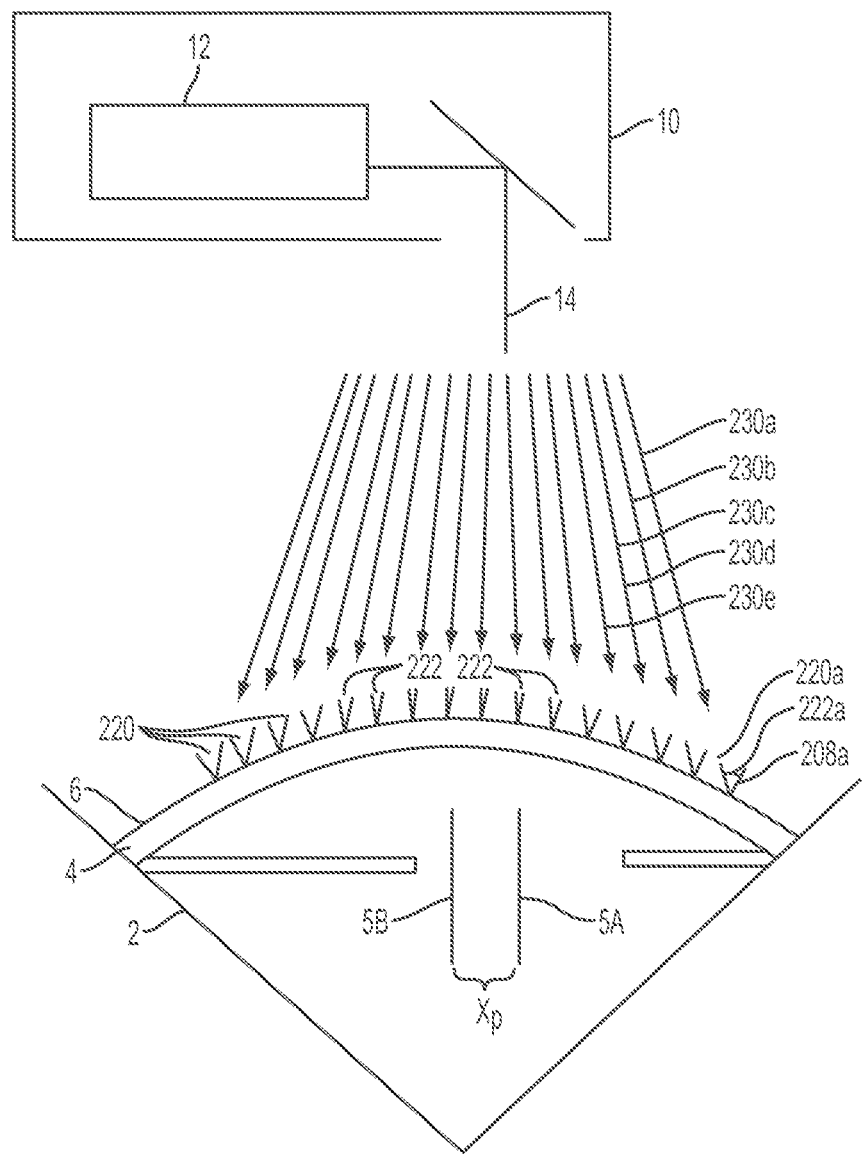
FIG. 9 Illustrates angles of incidence of several rays of a laser beam incident on a surface of a cornea in accord with an embodiment of the present invention.

A surgery and an optical tissue surface measurement are centered about a pupil of an eye as illustrated in FIG. 9. The center of the pupil 5A of the eye has an associated line of sight passing through the cornea of the eye as a patient looks at a fixation target. A line of sight is also referred to as a chief ray. A wavefront measurement of an eye is commonly centered about a pupil of an eye. A topography system generally has a central coordinate reference near an apex of the cornea 5B. A topography system may use any reference point as a coordinate center. Surface normal vectors are desirably calculated in relation to a center of the pupil. A pupil center in a topography system measurement reference system may be expressed as $(X_p, Y_p)$. A separation distance $X_p$ from the apex of the cornea 5B to the center of the pupil 5A is illustrated in FIG. 9. In a coordinate system centered about the pupil, surface normal vectors are represented as N(x',y') where $$x'=x-X_p \text{ and}$$

$$y'=y-Y_p.$$

A pupil-centered vector field N(x',y') is used to derive a local incident angle map Θ(x',y') as a function of local position on a surface of an eye. The local incident angle map Θ(x',y') describes a local angle at which a laser beam strikes a surface.

As illustrated in FIG. 9, the laser system 10 has the laser 12 that emits the laser beam 14 as described above. Several rays 230a to 230e of the laser beam 14 are illustrated. A local angle of the ray 230a of the laser beam 14 incident on the cornea is illustrated as a ray normal vector 220a. The ray normal vector 220a representing an angle of a laser beam is preferably a normalized vector (i.e. has a magnitude of one). Several ray normal vectors 220 of a map of ray normal vectors are illustrated in FIG. 9. Mathematically, a map of ray normal vectors is expressed as r(x',y'). A map of ray normal vectors is readily calculated for any laser system with a ray tracing program. A map of ray normal vectors is calculated in relation to an optical axis of a laser system 10 that is aligned with a center, preferably the pupil center 5A, during surgery.

The local incident angle map Θ(x',y') describes a local angle between a surface normal vector and a local angle of a laser beam incident on an eye. The local incident angle map Θ(x',y') is used to determine local ablation properties of a tissue. For each of several local incident angles, a local tissue ablation property is determined. A treatment table is generated based at least in part on a local ablation property.

Several local incident angles 222 of the local incident angle map Θ(x',y') are illustrated in FIG. 9. A local incident angle 222a between a local surface normal vector 208a and a local ray normal vector 220a of a laser beam is illustrated. The local angle of incidence 222a is related to a dot product projection of the local ray normal vector 220a and the surface normal vector 208a. The local incident angle map Θ(x',y') is calculated from a dot product projection of surface normal vectors 208 and several ray normal vectors 220 as:

$$\Theta(x',y')=\cos^{-1}[r(x',y')n(x',y')].$$

Figure 9A:
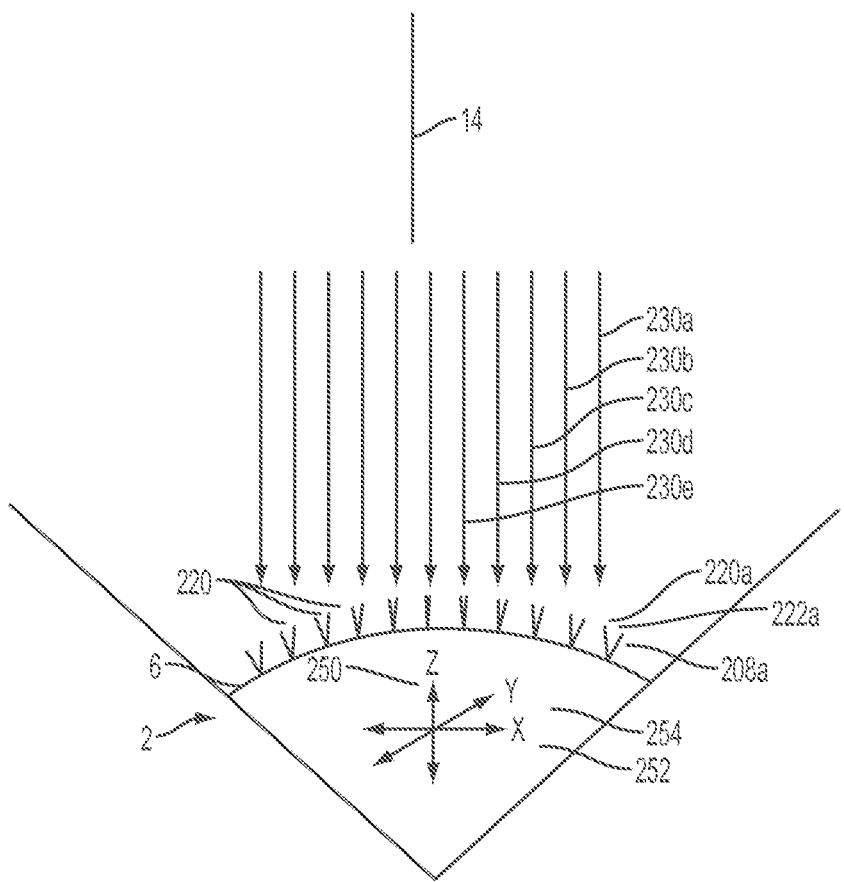
FIG. 9A illustrates angles of incidence of several parallel rays of a laser beam incident on a surface of a cornea in accord with an embodiment of the present invention.

In an embodiment illustrated in FIG. 9A, several rays 230a to 230e of the laser beam 14 are incident on the surface 6 of the cornea of the eye 2. Several rays 230a to 230e of the laser beam 14 are parallel. A Z axis 250 is perpendicular to a plane of X and Y coordinate references 252, 254 respectively. The Z axis 250 is parallel to rays 230a to 230e. In this embodiment, the Z axis 250 is parallel to several local ray normal vectors 220 and the ray normal vector 220a. The local angle of incidence 222a is related to a dot product projection of the local ray normal vector 220a and the surface normal vector 208a as described above. As ray normal vectors 220 are parallel to the Z axis 250, the local angle of incidence is related to a dot product projection of Z axis 250 and a surface normal vector. the local incident angle map Θ(x',y') may be calculated as $$\Theta(x',y')=\cos^{-1}(N_{z(x',y')}/\|N\|)$$

where $N_z$ is the z-component of the surface normal and $\|N\|$ is the magnitude of the surface normal vector.

Figure 10:
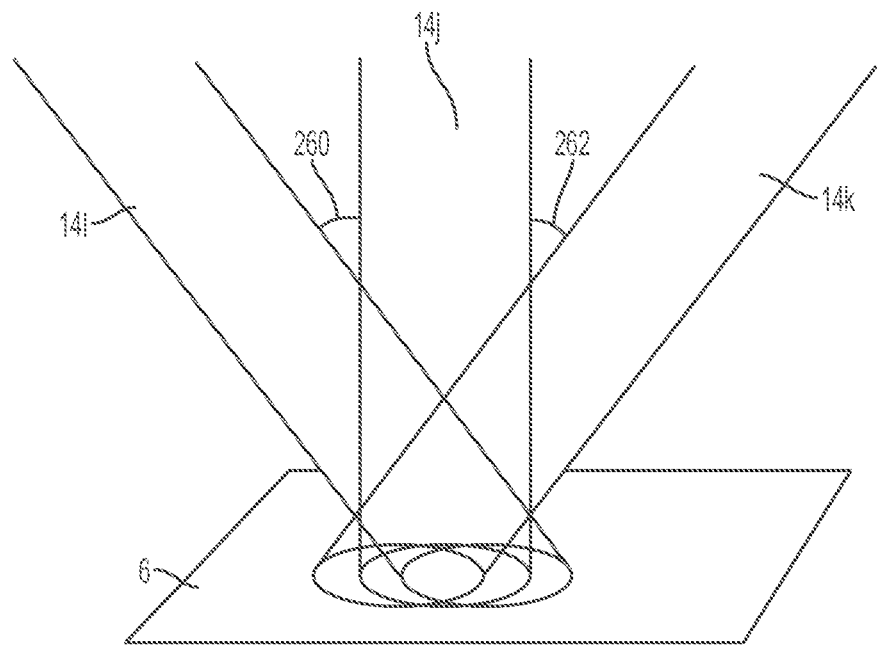
FIG. 10 illustrates laser beams simultaneously overlapping on a surface of a cornea in accord with an embodiment of the present invention.

In an embodiment illustrated in FIG. 10, the laser beam 14 as described above is divided into several smaller laser beams, for example beams 14I, 14J and 14K. The laser beams 14I, 14J and 14K overlap and are incident on the surface 6 of the cornea. The laser beams 14I and 14J are separated by an angle 260. The laser beams 14J and 14K are separated by an angle 262. Systems and methods for multiple beam laser sculpting are described in U.S. Pat. No. 6,331,177, the full disclosure of which is incorporated herein by reference.

Figure 10A:
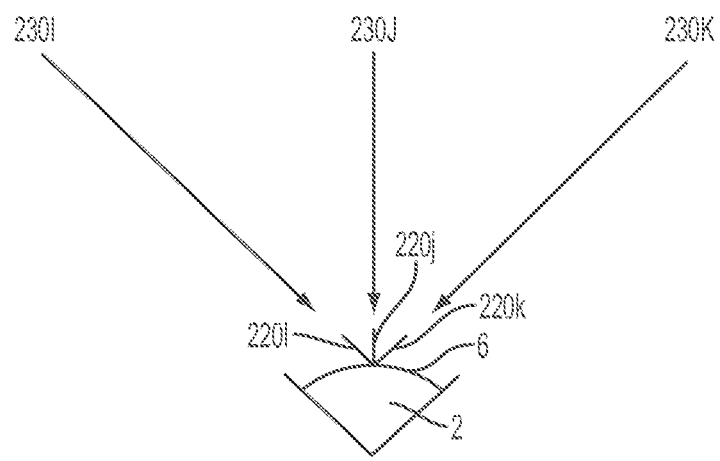
FIG. 10A illustrates angles of incidence of simultaneously overlapping rays of laser beams incident on a surface of a cornea in accord with an embodiment of the present invention.

The laser beams 14I, 14J and 14K include rays 230I, 230J and 230K incident on a common location on the surface 6 of the cornea of the eye 2, as illustrated in FIG. 10A. The ray normal vectors 220I, 220J and 220K describe an angular orientation of each of the beams 14I, 14J and 14K, respectively at a common location on the surface 6. An angle of incidence between each ray and a surface normal vector is calculated as described above. In some embodiments, the angles 260 and 262 are small and the ray normal vectors 220I, 220J and 220K are assumed to be accurately represented by a single ray normal vector, for example ray normal vector 220J.

A local angle of incidence of a laser beam on a corneal surface is used to determine local ablation properties. An amount of light locally transmitted into a tissue is related to the angle of incidence of the laser beam. Several factors contribute to the amount of light transmitted into the tissue. Reflection of light energy from a surface is one such factor. Another factor is an effective increase in a size of surface area irradiated by the laser beam.

An effective fluence of a light beam applied on a surface changes with an angle of incidence of a light beam. A change in an applied fluence with a change in an angle of incidence is referred to as a cosine effect. A beam incident on a surface illuminates an increased area as an angle of incidence increases. For a fixed amount of energy along a cross sectional dimension of a laser beam, an increase in an illuminated area will decrease an amount of energy per unit area applied to a tissue. An effective fluence applied to a surface changes as a cosine of an angle of incidence. For example, a laser beam having a cross sectional diameter of 1 mm and a fluence of 160 mJ/cm$^2$ will irradiate a 1 mm cross sectional diameter of tissue with a fluence of 160 mJ/cm$^2$ when an angle of incidence is 0. However, a laser beam having a cross sectional diameter of 1 mm and oriented at 45 degrees to a surface will irradiate a cross section of tissue having a length of 1.4 mm along a first dimension and a length of 1 mm along a second dimension. An effective fluence applied to a surface will decrease to 110 mJ/cm$^2$.

Figure 11:
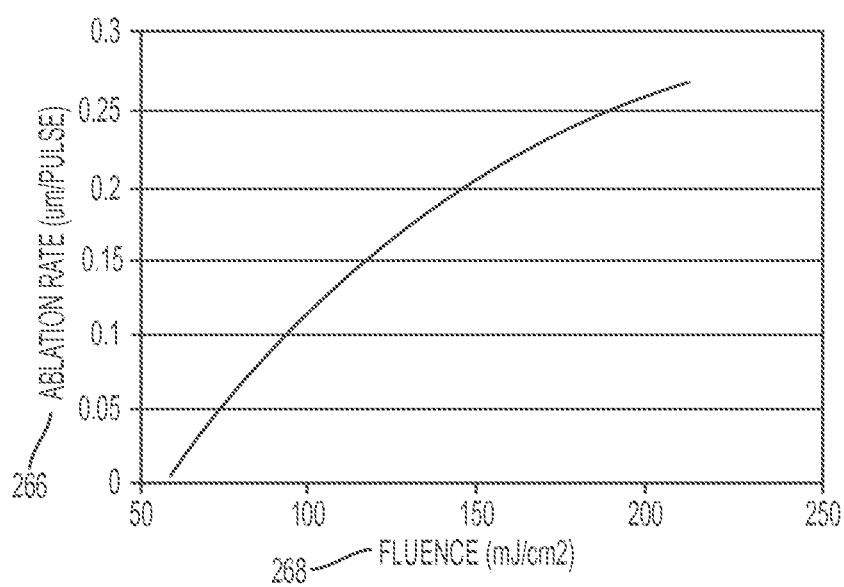
FIG. 11 illustrates an ablation rate of a corneal tissue as related to a fluence of a laser beam applied to a tissue surface.

As illustrated in FIG. 11, an amount of tissue ablated with a pulse of a laser beam depends at least in part on an amount of energy per unit area applied to a tissue. An ablation rate 266 changes with a fluence 268 of light energy applied to an eye with a pulse of a laser beam applied. At a fluence 268 of about 160 mJ/cm$^2$, an ablation rate 266 is illustrated as about 0.23 um per pulse for a laser beam at normal incidence. At a fluence 268 of 110 mJ/cm$^2$, an ablation rate 266 is illustrated as about 0.11 um per pulse for a laser beam at normal incidence. Systems and methods for measuring tissue ablation rates are known, and alternate embodiments may use a different ablation rate 266 for a similar amount of applied fluence 268.

Amounts of light energy reflected from a surface and transmitted through a surface into a tissue change with a change in an angle of incidence of a light beam. An amount of light energy transmitted into a tissue is calculated with Fresnel formulae. These formulae are known, and use an index of refraction and an angle of incidence to determine an amount of light energy penetrating into a tissue. For an excimer laser as described above polarization is random. In alternate embodiments a laser beam is polarized. A fraction of light energy transmitted into a tissue is determined by a transmissivity expressed as $$T(\Theta_i) = \{[(\sin 2\Theta_i \sin 2\Theta_t)/(\sin^2(\Theta_i+\Theta_t)\cos^2(\Theta_i-\Theta_t))] + [(\sin 2\Theta_i \sin 2\Theta_t)/(\sin^2(\Theta_i+\Theta_t))]\}/2$$

for a randomly polarized light beam, where $\Theta_i$ is an angle of incidence of a light beam and $\Theta_t$ is a transmitted angle of light beam. The angle of incidence $\Theta_i$ of a light beam is related to the transmitted angle $\Theta_t$ by Snell's law. For corneal tissue, an index of refraction is about 1.377. The transmitted angle $\Theta_t$ calculated from Snell's law is expressed as:

$$\sin \Theta_t = \sin \Theta_i/1.377,$$

where $\Theta_i$ is the angle of incidence of a light ray.

Figure 12:
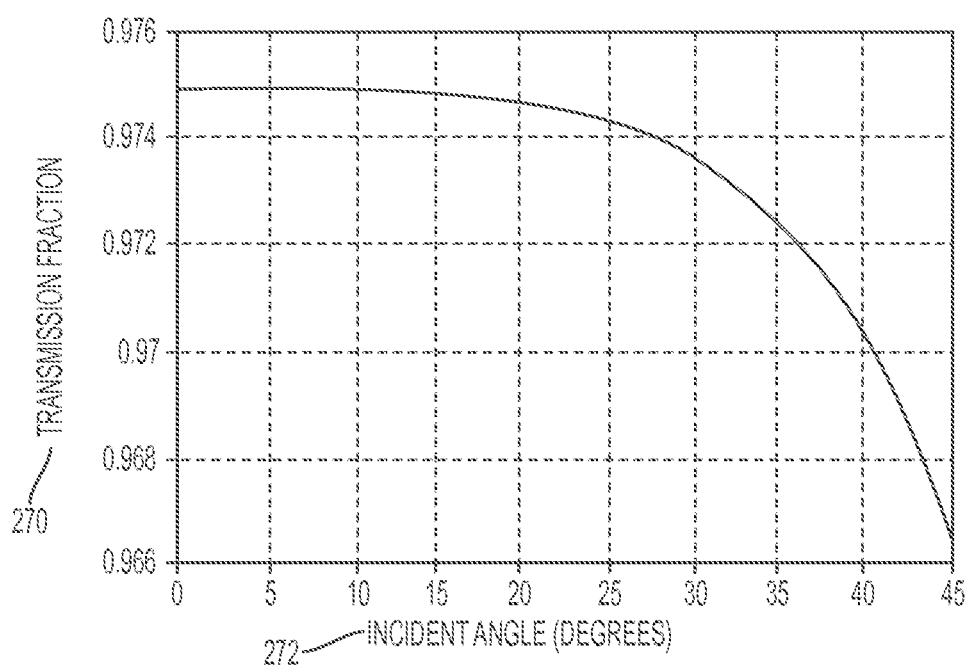
FIG. 12 illustrates a fraction of a light energy transmitted into a corneal tissue as related to an angle of incidence of a laser beam.

A fraction 270 of energy transmitted into the corneal tissue is illustrated in FIG. 12. The fraction 270 of energy transmitted into the tissue changes with an angle of incidence 272. For an angle of incidence 272 of 0, the fraction 270 of light energy transmitted into a tissue is illustrated as 0.975, or about 98%. For an angle of incidence 272 of 45 degrees, a fraction 270 of energy transmitted is illustrated as 0.966, or about 97%.

Figure 13:
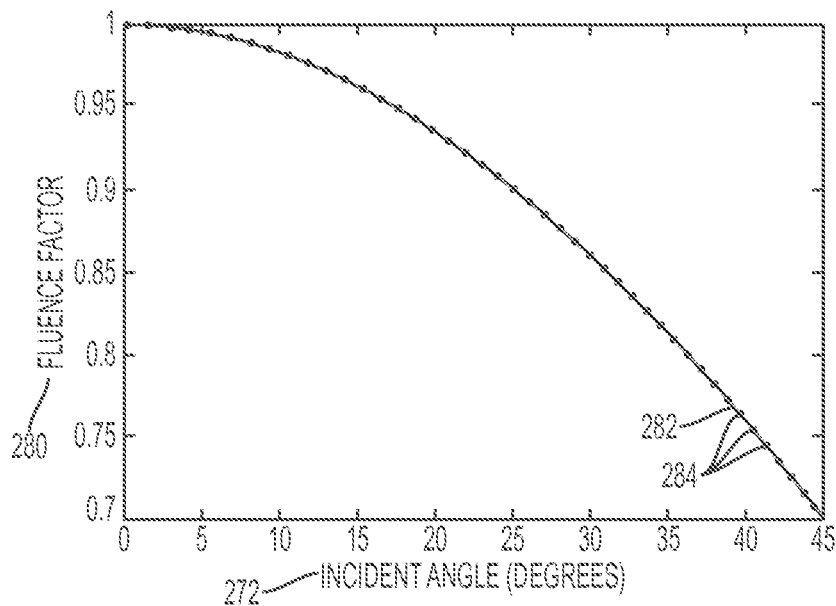
FIG. 13 illustrates a fluence factor as related to an incident angle of a laser beam in accord with an embodiment of the present invention.

A fluence factor 280 is determined for the angle of incidence 272 as illustrated in FIG. 13. The fluence factor is used to determine an applied local tissue fluence of a laser beam. The fluence factor 280 is a fraction of cross sectional beam energy transmitted through a tissue surface and varies with the incident angle 272. A fluence factor 280 includes a "cosine effect" and a transmission fraction 270 as described above. The fluence factor 280, including both a cosine projection and a transmission fraction 270, is illustrated with several dots 284. In some embodiments, a fluence factor may include a cosine projection of a beam onto a surface and assume reflectance to be uniform across a mapped cornea, as illustrated with a solid line 282. Local tissue fluence is determined at a location by multiplying a fluence factor and a fluence of a laser beam. For a laser beam having a cross-sectional fluence of 160 mJ/cm$^2$ at normal incidence to a surface and a fluence factor of 0.9 at 25 degrees, a tissue fluence is a product of 0.9 and 160 equaling 144 mJ/cm$^2$. Other embodiments may use a laser beam having a Gaussian energy intensity profile distribution. The local fluence may be calculated by multiplying a fluence factor by a local energy intensity at normal incidence.

For a local angle of incidence of a laser beam, a local fluence transmitted into a tissue is determined. A local tissue ablation rate is determined from the local fluence transmitted into the tissue using a tissue ablation rate as related to fluence applied at normal incidence as described above.

Figure 14:
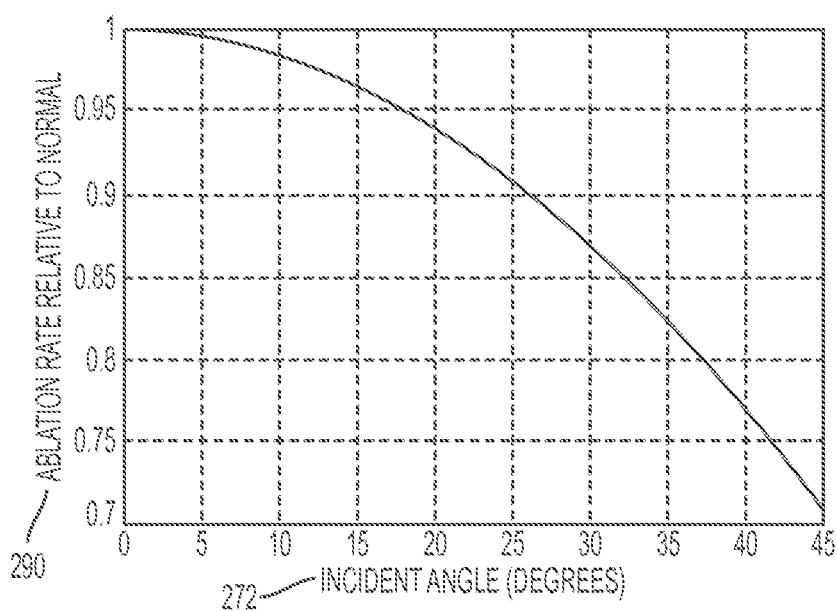
FIG. 14 illustrates an ablation rate relative to an ablation rate at normal incidence in accord with an embodiment of the present invention.

An ablation rate relative to ablation at normal incidence 290 is illustrated in FIG. 14 and varies with an incident angle 272. In an embodiment using a fluence factor, a laser beam fluence and tissue ablation rate as described above, a local tissue ablation rate relative to the tissue ablation rate at normal incidence may be determined. This local tissue ablation property may be used to adjust a laser beam treatment. In some embodiments, the local tissue ablation rate relative to ablation at normal incidence may be accurately determined by a cosine function of an angle of incidence, for example at small angles of incidence.

Figure 15:
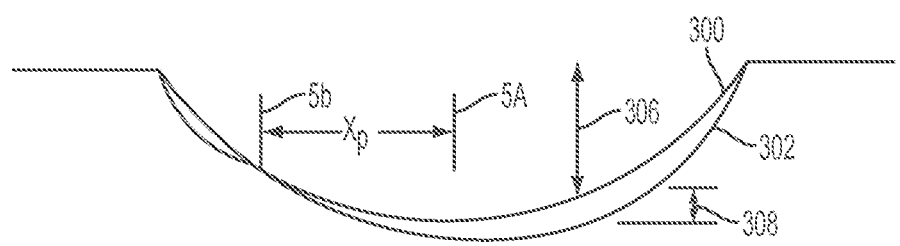
FIG. 15 illustrates a desired predetermined ablation shape as a first virtual surface warped to form a second virtual surface in accord with an embodiment of the present invention.

In one embodiment, a predetermined intended ablation shape of tissue removed from a corneal tissue is adjusted to compensate for local ablation properties as illustrated in FIG. 15. In some embodiments, an adjustment of a virtual ablation shape from a first virtual shape to a second virtual shape may be referred to as warping of an ablation target. A predetermined shape of ablation is stored in a memory of a processor as a first virtual shape 300. A local incident angle map is used to determine a map of local ablation properties, for example a map of local ablation rate relative to an ablation rate at normal incidence as described above. A first virtual shape 300 is adjusted by dividing a depth of a first virtual shape 300 by an amount of relative ablation to form a second virtual shape 302. For example, the first virtual shape 300 has a depth 306 of ablation of 10 um at a location. A map of local ablation properties determines relative ablation to be 0.9 locally. The second virtual shape 302 has a local depth of ablation of 11 um that has increased by an amount 308 of 1 um. A treatment plan is determined from the second virtual shape 302 and listed in a treatment table as described above. As a series of pulses is applied to an eye, a shape of ablated tissue matches the first virtual shape 300.

Figure 16:
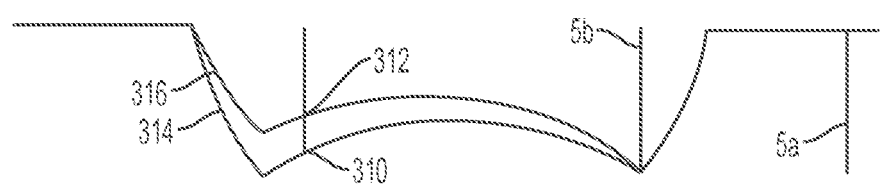
FIG. 16 illustrates a crater of material removed with a single pulse of a laser beam as a first virtual surface warped to form a second virtual surface in accord with an embodiment of the present invention.

In another embodiment, a simulated shape of material removed with each pulse of a laser beam is adjusted based on local ablation properties as illustrated in FIG. 16. At least one crater of material removed with a single pulse of a laser beam is stored in a memory of a processor as a first virtual surface 314. Systems and methods for determining shapes of tissue removed with a laser beam are described in U.S. Pat. Nos. 6,315,413 and 6,302,876, the full disclosures of which are incorporated herein by reference. During a treatment, a final ablated shape of material removed from a surface is a summation of individual craters of tissue removed with each pulse of a series of laser beam pulses. To determine a simulated shape of an ablation, each simulated crater of tissue removed in a series of pulses is adjusted by local ablation properties. As illustrated in FIG. 16, a crater described by a first virtual surface 314 is adjusted using local ablation properties to form a second virtual surface 316. The second virtual surface 316 illustrates a crater of material removed as adjusted based on local ablation properties. A center of a pupil is illustrated at 5A as described above. As illustrated for a treatment centered about a pupil, the first and second virtual surfaces 314 and 316 respectively are displaced from a treatment center as may occur during a scanning treatment.

Often, a local fluence of light energy transmitted into a tissue is determined and a local depth of ablation determined as described above. In some embodiments, a depth of ablation may be adjusted by a factor such as an ablation rate relative to an ablation rate at normal incidence as described above. A depth of ablation 310 at a location of the first virtual surface 314 is decreased to a second depth of ablation 312 in the second virtual surface 316 as adjusted based on local ablation properties. A center of a cornea at normal incidence to a laser beam ray is illustrated at 5B as described above. At normal incidence, the depth of the first virtual surface 314 matches the depth of the second virtual surface 316. To determine a predetermined shape of tissue removed by a series of laser beam pulses, several craters are adjusted based on local ablation properties and combined to determine a total shape of material removed. Each crater of a treatment is adjusted based on local ablation properties and a treatment plan is calculated and listed as treatment table as described above.

Figure 17:
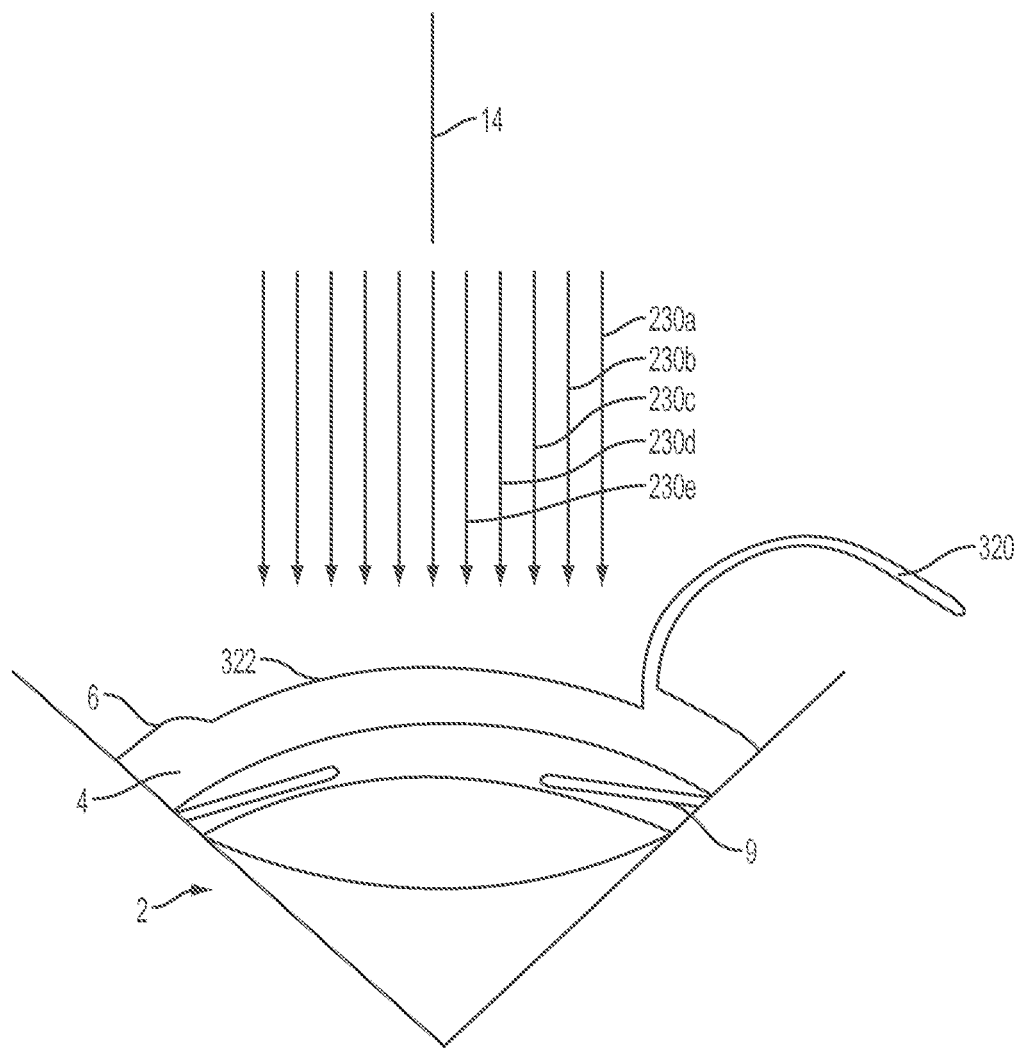
FIG. 17 illustrates a laser beam incident upon a corneal surface during a LASIK surgical procedure in accord with an embodiment of the present invention.

In one embodiment, a LASIK surgical eye procedure is performed on an eye as illustrated in FIG. 17. The eye 2 has a cornea 4. Several rays 230A-230E of the laser beam 14 are incident on a surface of a cornea as described above. Several local angles of incidence of rays of laser beam 14 are determined as described above. Local tissue ablation properties are determined at least in part in response to local incident angles as described above. A flap of corneal tissue 320 is resected from the cornea 4, exposing a bed of stromal tissue 322. In a preferred embodiment, several local angles of incidence are determined before a flap of corneal tissue 320 is resected. In some embodiments, several local angles of incidence and local tissue ablation properties may be determined after a flap of corneal tissue 320 is resected. A laser beam treatment forms a desired ablation shape in the cornea 4 as described above. After ablation, the flap 320 is repositioned over a bed of stromal tissue 322.

Measurement Data Assimilation

According to some embodiments of the present invention, measurement data assimilation is based on a Kalman-Bucy technique for corneal topography and/or wavefront measurements to provide a statistically optimal estimate of a measured field and a measure of the quality of the measured field. This method combines measured corneal elevations with a priori information, including mean and covariance of Zernike amplitudes for a measured surface known prior to the measurement. A priori mean and covariance before any measurements can be estimated from available data for a general population. This technique yields a statistically optimal estimate of Zernike amplitudes that represent weighted averages of prior estimates and measured values. Measured values that deviate farther from a priori corneal shape can be included with smaller weighting. This provides the technique with robustness for measurement outliers. The data assimilation also yields an estimate for a post-measurement covariance matrix of Zernike amplitudes. Variances of Zernike amplitudes provide a measure of the measurement quality.

Figure 18A:
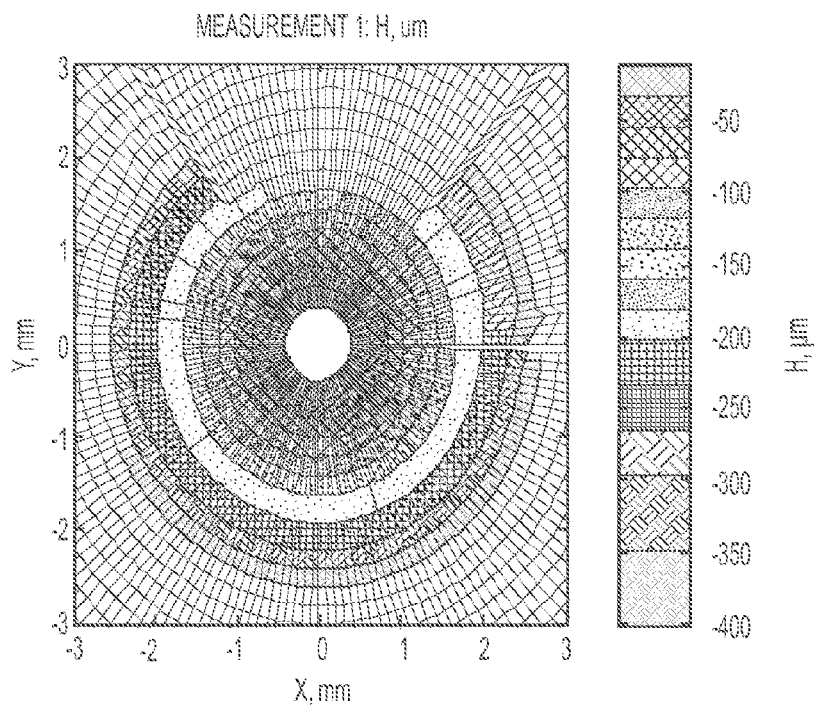
FIGS. 18A and 18B are graphs illustrating corneal elevation measurements.
Figure 18B:
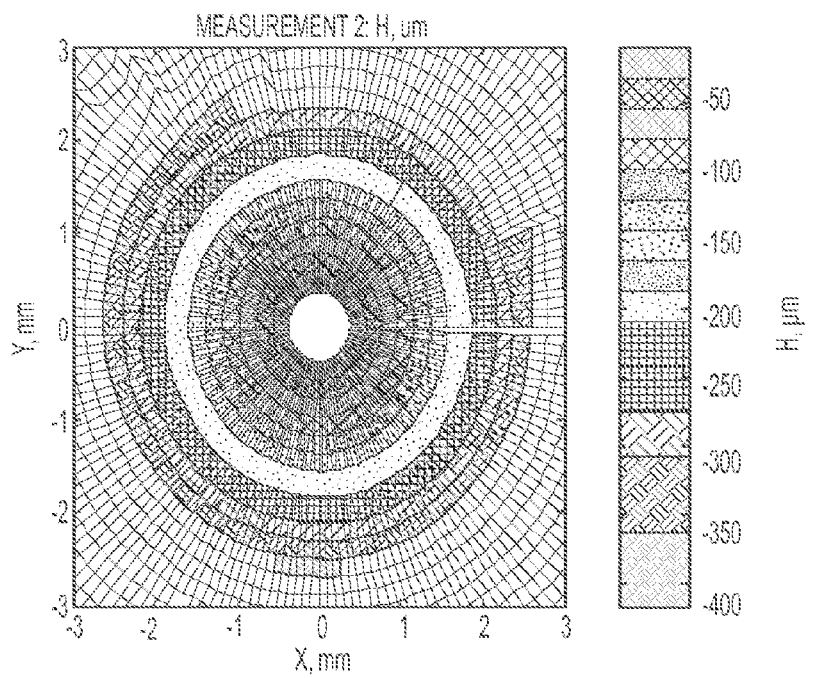

With respect to corneal topography, every topography measurement yields a two-dimension field of corneal elevations and typically contains some gaps and inaccuracies. FIGS. 18A and 18B are graphs illustrating corneal elevation measurements of an eye using a Humphrey® Atlas™ Corneal Topography System from ZEISS HUMPHREY SYSTEMS.

Figure 19A:
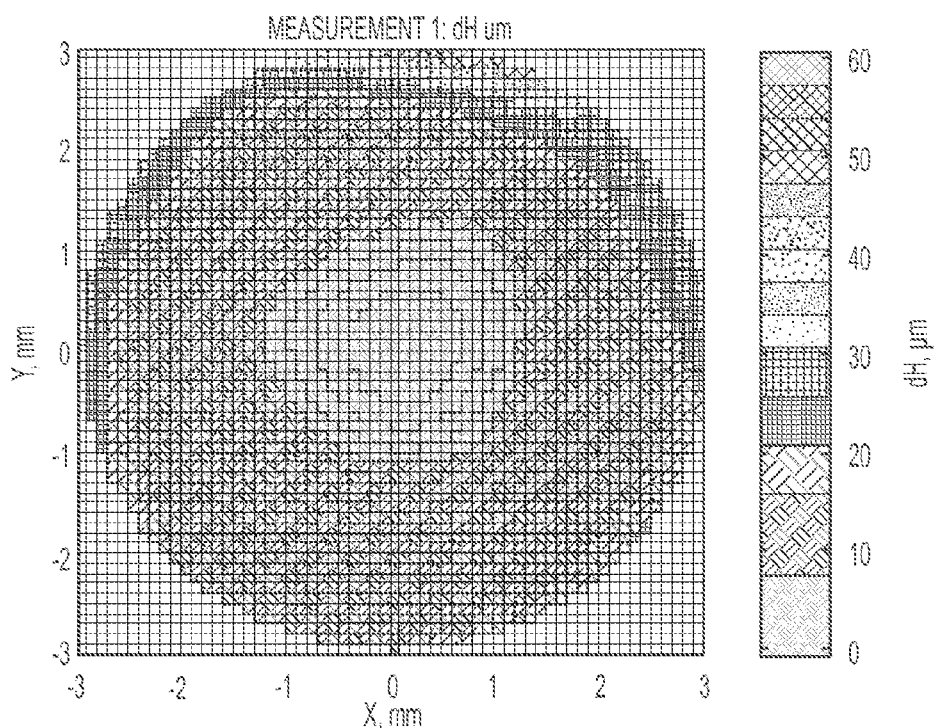
FIGS. 19A and 19B are graphs illustrating deviations of the corneal elevation measurements shown in FIGS. 18A and 18B from an average corneal shape, respectively.
Figure 19B:
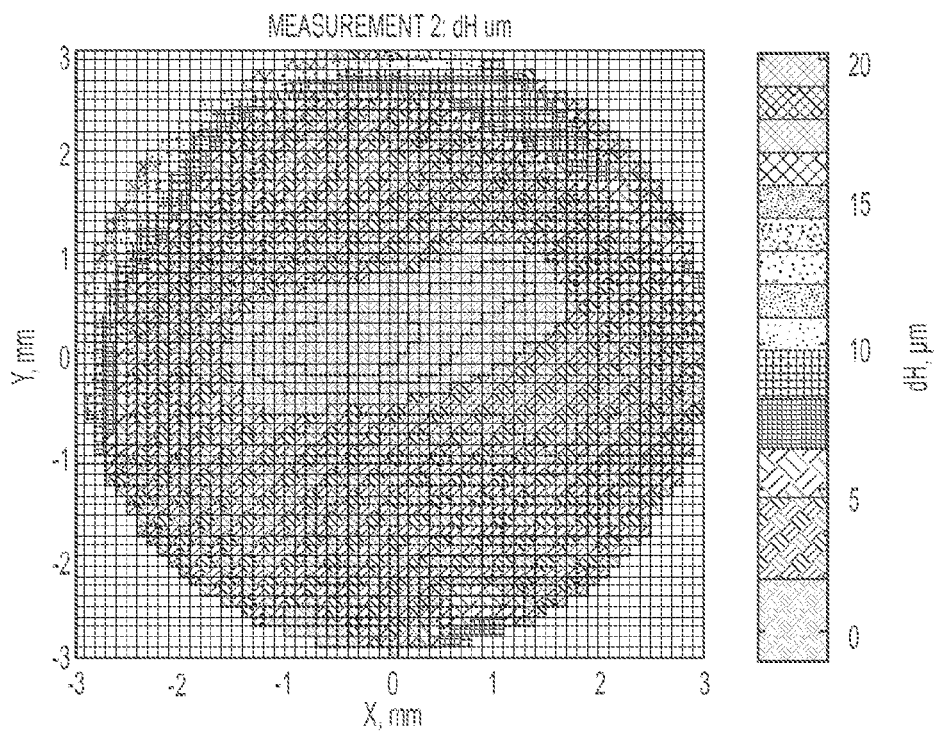
Figure 20A:
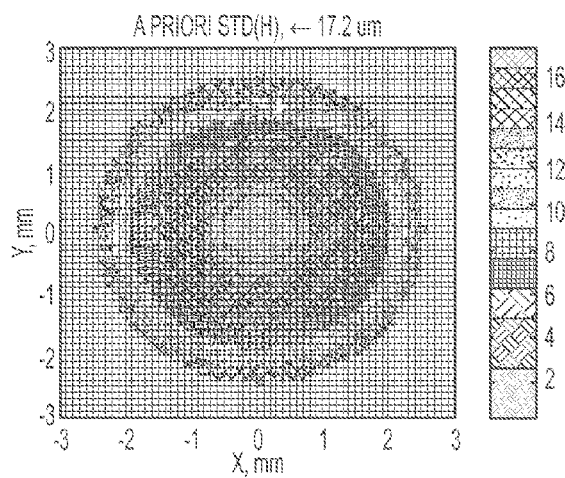
FIG. 20A is a graph illustrating corneal elevation uncertainty for an a priori measured corneal shape, according to embodiments of the present invention.
Figure 20B:
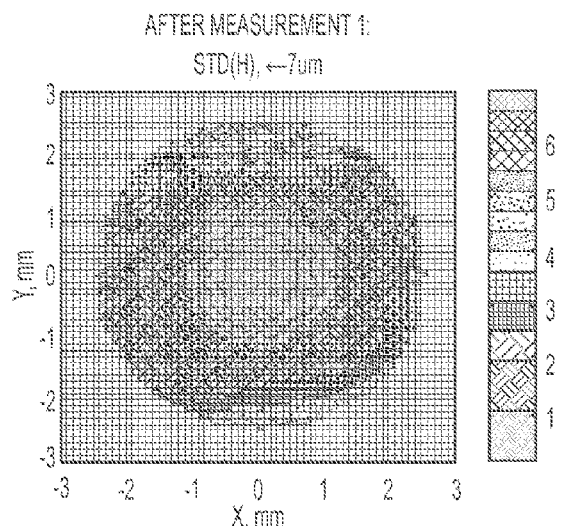
FIG. 20B is a graph illustrating corneal elevation uncertainty for a post-measurement corneal shape, according to embodiments of the present invention.
Figure 21:
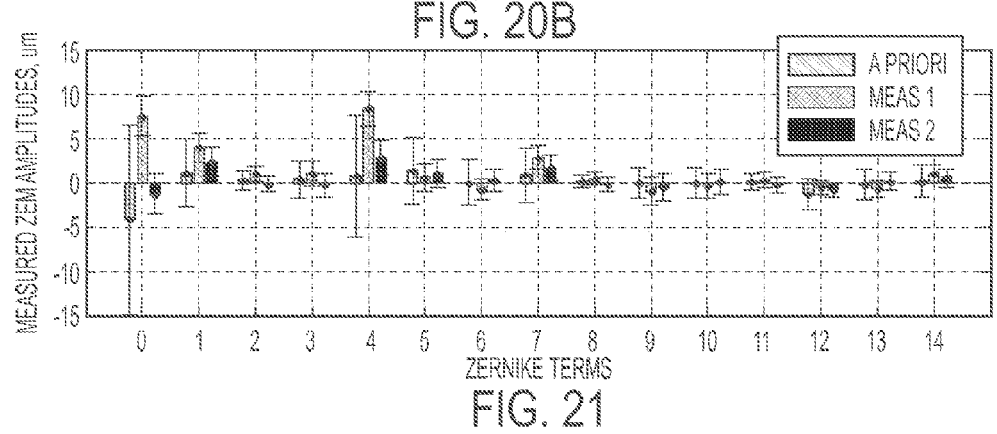
FIG. 21 is a chart illustrating a priori and measured Zernike amplitudes, according to embodiments of the present invention.

Estimated Zernike amplitudes allow reconstruction of the corneal elevation field within the circular area used for Zernike decomposition. FIGS. 19A and 19B are graphs illustrating deviations of the corneal elevation measurements shown in FIGS. 18A and 18B from an average corneal shape, respectively. The estimated covariance matrix allows for an estimate of the uncertainty of corneal elevations and Zernike amplitudes. FIG. 20A is a graph illustrating corneal elevation uncertainty for an a priori measured corneal shape. FIG. 20B is a graph illustrating corneal elevation uncertainty for a post-measurement corneal shape. FIG. 21 is a chart illustrating a priori and measured Zernike amplitudes.

Applying the Kalman-Bucy technique, two estimates of measured values weighted by respective variances are combined. As a result, larger random deviations from the prior estimate make relatively smaller contribution to the measurement result. The measurement results are thus more robust and statistically optimal. This method extracts maximum available information from all of the measurements combined as well as from a priori knowledge of the measured field.

Data assimilation, based on the Kalman-Bucy algorithm, has the following advantages compared to a simple averaging of measured data: statistically optimal combination of multiple measurements; assimilation of a priori information; protection from measurement outliers; and an objective estimate of measurement accuracy.

Statistics of Human Corneal Topography

Figure 22A:
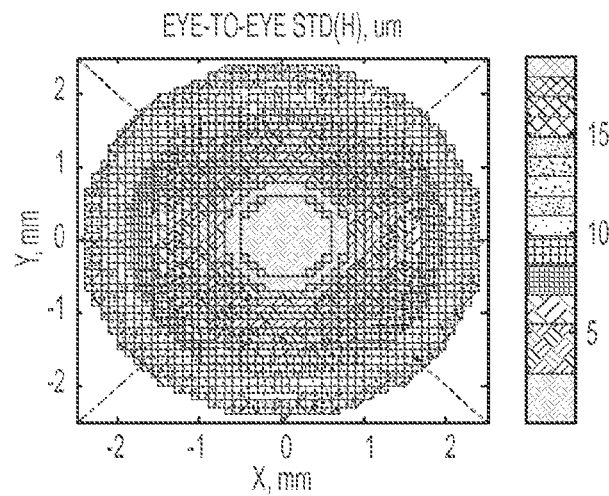
FIG. 22A is graph illustrating standard deviation of a corneal elevation field for different eyes, according to embodiments of the present invention.
Figure 22B:
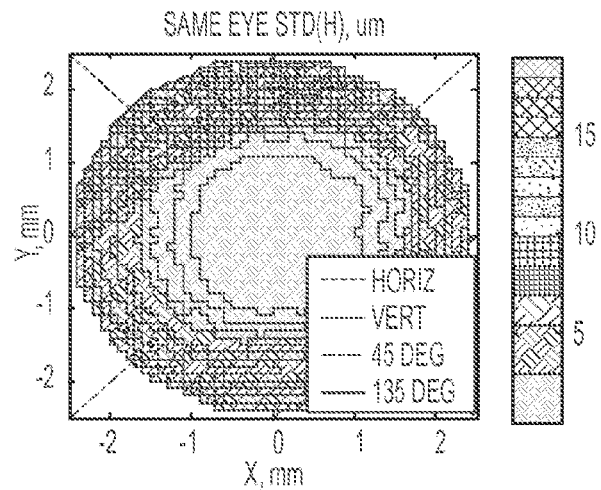
FIG. 22B is a graph illustrating standard deviation of a corneal elevation field for the same eye, according to embodiments of the present invention.
Figure 23A:
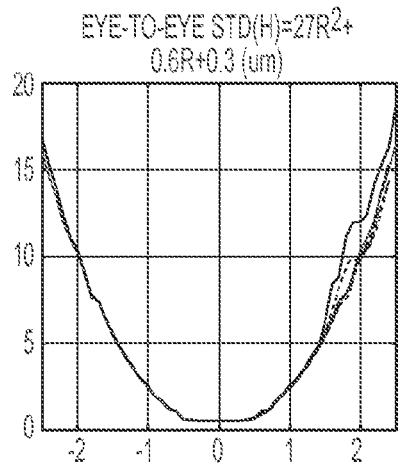
FIG. 23A is a graph illustrating radial dependence for the standard deviation of corneal elevation shown in FIG. 22A.
Figure 23B:
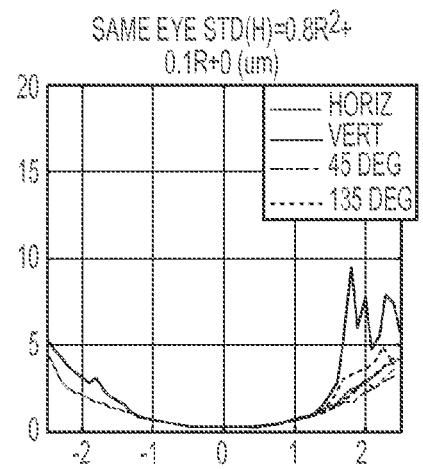
FIG. 23B is a graph illustrating radial dependence for the standard deviation of corneal elevation shown in FIG. 22B.
Figure 24:
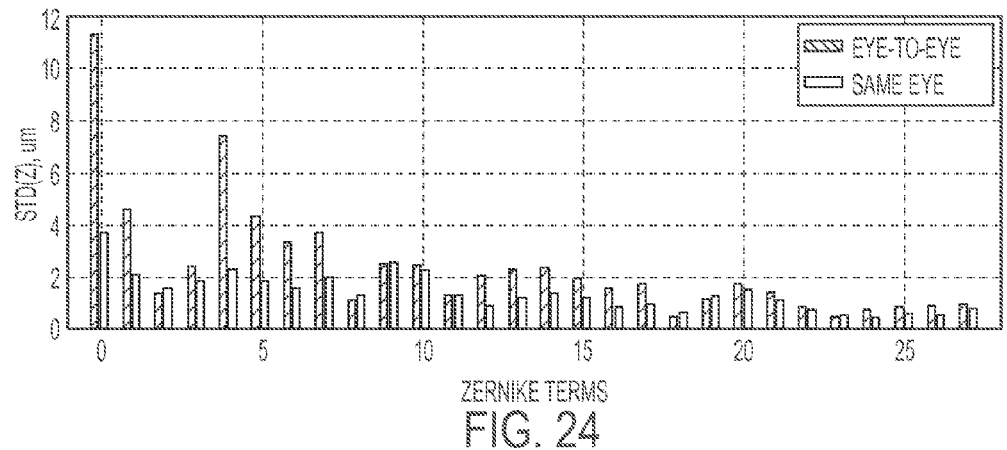
FIG. 24 is a chart illustrating standard deviation of Zernike amplitudes for the corneal elevation fields shown in FIGS. 22A and 22B.
Figure 25:
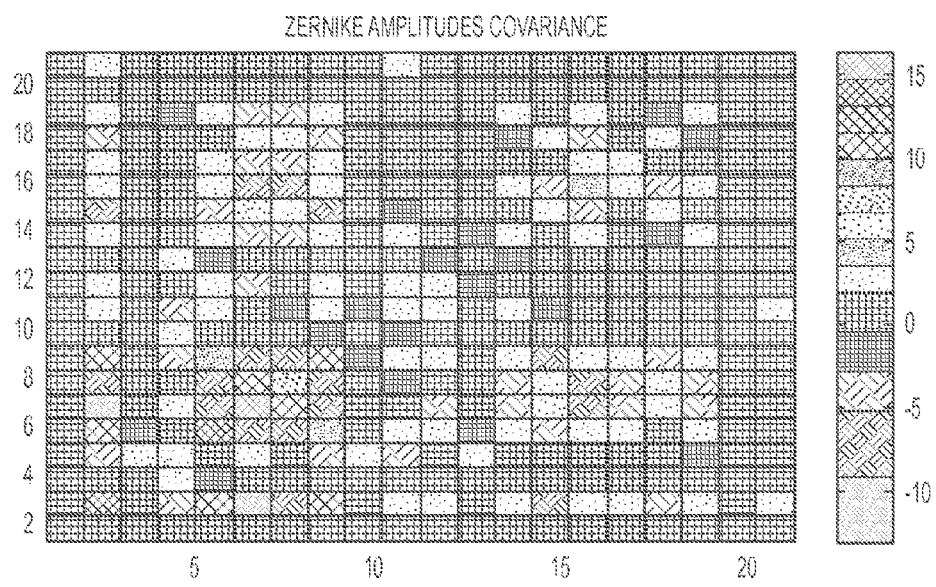
FIG. 25 is a graph illustrating covariance of Zernike amplitudes for corneal elevation, according to embodiments of the present invention.

Corneal topography data from a population of pre-operational eyes, some of which had multiple measurements, can be used to determine statistics for two types of random fluctuations of measurement data: variations of multiple measurements for the same; and eye-to-eye differences (variations of measurement averages between different eyes). FIG. 22A is graph illustrating standard deviation of a corneal elevation field for different eyes based on variations of measurement averages between the different eyes. FIG. 22B is a graph illustrating standard deviation of a corneal elevation field for multiple measurements of the same eye. FIG. 23A is a graph illustrating radial dependence for the standard deviation of corneal elevation shown in FIG. 22A. FIG. 23B is a graph illustrating radial dependence for the standard deviation of corneal elevation shown in FIG. 22B. FIG. 24 is a chart illustrating standard deviation of Zernike amplitudes for the corneal elevation fields shown in FIGS. 22A and 22B. FIG. 25 is a graph illustrating covariance of Zernike amplitudes for corneal elevation.

Kalman-Bucy Technique for Corneal Topography Data Processing

In one embodiment, a method of sequential assimilation of corneal topography measurements combines each measurement of a corneal elevation field with results of previous topography measurements (e.g., archived data) for the same eye and includes a priori statistical information of corneal shape. For each corneal topography studied, the Kalman-Bucy technique yielded an estimate of Zernike amplitudes and a corresponding covariance matrix. These estimates resulted in a reconstructed corneal elevation map without gaps within a circular area used for Zernike decomposition, as well as a map of measurement uncertainty.

The sequential estimation method is designed to combine a priori statistical information with one or more measurements of a system, described by a M×1 parameter vector, A. We assume that the system is governed by a linear system $$h = \hat{G}A + \tilde{h}, \quad (B1)$$

where h is the D×1 vector of observations, $\hat{G}$ is the coefficients matrix of a linear observation model, and $\tilde{h}$ is the vector of measurement errors.

For corneal topography measurements the corneal elevation shall be the vector of observations, h, and Zernike decomposition of elevation field is used as a linear model:

$$h(x, y) = \sum_{i=0}^{N} A_i \cdot Z_i(x, y), \quad (B2)$$

where $Z_i(x,y)$ are Zernike polynomials and $A_i$ are the amplitudes of Zernike decomposition.

Thus if the elevation field is defined on a set of points, $(x_k, y_k)$, the model will be defined by the M×M matrix, $$G_{i,k} = Z_i(x_k, y_k). \quad (B3)$$

The Kalman-Bucy algorithm, applied to corneal topography measurements, assimilates each measurement by combining the measured data (cornea elevations field) with the prior estimate of mean vector, $A_i^{(j)}$, and covariance matrix for Zernike amplitudes, $C_{ik}^{(j)} \equiv \langle A_i^{(j)} \cdot A_k^{(j)} \rangle$, as defined by the following formulas:

$$A_i^{(j+1)} = A_i^{(j)} + \hat{K}^{(j)} \cdot [h_k^{(j)} - G_{i,k} \cdot A_i^{(j)}] \quad (B4)$$

$$\hat{C}^{(j+1)} = \{\hat{I} - \hat{K}^{(j)} \cdot \hat{G}^{(j)}\} \cdot \hat{C}^{(j)}, \quad (B5)$$

where I is the identity matrix having dimensions M×M, $$\hat{K}^{(j)} = \hat{C}^{(j)} \cdot G^T \cdot \hat{F}^{(j)} \quad (B6)$$

is the Kalman-Bucy gain, and $$\hat{F}^{(j)} = \{\hat{G} \cdot \hat{C}^{(j)} \cdot \hat{G}^T + \hat{N}\}^{-1} \quad (B7)$$

is a D×D matrix. The D×D matrix $\hat{N}$ is the covariance matrix of measurement errors.

Formulas (B4-B7) provide a statistical optimal estimation of the parameter vector, $A_i^{(j-1)}$, and its covariance matrix, $\hat{C}^{(j+1)}$, after the j-th measurement is assimilated together with prior j−1 measurements.

This method gives us an iterative algorithm of sequential assimilation of corneal topography measurements. The first step in the iterative sequence starts with an a priori estimate of mean parameter vector (Zernike amplitudes of corneal elevation) and the corresponding covariance matrix. These a priori values for corneal topography, as well as the covariance matrix $\hat{N}$ of the elevations measurement errors, can be derived from statistics of general population, as previously mentioned.

Once we have the covariance matrix for Zernike amplitudes, we can calculate variance of the corneal elevation field as follows:

$$\operatorname{Var}(h(x, y)) = \left\langle \left( \sum_i A_i \cdot Z_i(x, y) \right) \cdot \left( \sum_k A_k \cdot Z_k(x, y) \right) \right\rangle \quad (B8)$$
$$= \sum_{i,k} C_{i,k} \cdot Z_i(x, y) \cdot Z_k(x, y).$$

EXAMPLE 1

With many topography fields measured for normal human eyes we can decompose each elevation field into Zernike series and evaluate the mean and variance of each amplitude. This will be the a priori information to input into the Kalman-Bucy filter together with the measurement data. The Kalman-Bucy filter will be applied according to the following formulas:

$$A_k^+ = A_k^- + \hat{K} \cdot \{H - \hat{G} \cdot A_k^-\}, \quad M_k^+ = \hat{K} \cdot \{\hat{I} - \hat{K}\hat{G}\} \cdot M_k^-.$$

Here $A_k^-, M_k^-$ and $A_k^+, M_k^+$ are the Zernike amplitudes and their covariance matrices prior and after assimilation of measurement data, respectively, H is the vector of measurement data (topography elevations), $\hat{G}$ is the operator of surface reconstruction from Zernike amplitudes (a surface defined on $x_i, y_1$ points can be computed from Zernike amplitudes and Zernike polynomials $\Phi_k(x_i, y_i)$ at these points as $$S_i = \sum_k A_k \Phi_k(x_i, y_i) \Bigg), \quad \hat{K} = \hat{M}^{-1} \hat{G}^T \hat{F}$$

is the Kalman-Bucy gain, $\hat{F} = \{\hat{G}M^-\hat{G}^T + \hat{N}\}^{-1}$, $\hat{N}$ is the data noise covariance matrix, and I is a unitary matrix.

Sequential measurements shall apply the same procedure to the prior measurement outcome, $A_k^-, M_k^-$. As a result, with each measurement assimilated the measured amplitudes approach closer to the true value and the measurement uncertainty decreases. Diagonal elements of the covariance matrix, $\hat{M}$, give us the estimate of uncertainty in the measured amplitude.

In some embodiments, the same method of sequential estimation can be applied to wavefront measurements, performed with an aberrometer, where a lenslet images of distorted spots yield noisy and incomplete data. Multiple measurements and Fourier decomposition are typically used there to re-construct the wavefront surface. Sequential estimation can provide a statistically optimal combination of sequential measurements and include a priori information. In some embodiments, the same method of sequential estimation can be applied to combinations of different measurements, such as wavefront and topography measurements.

EXAMPLE 2

Figure 26:
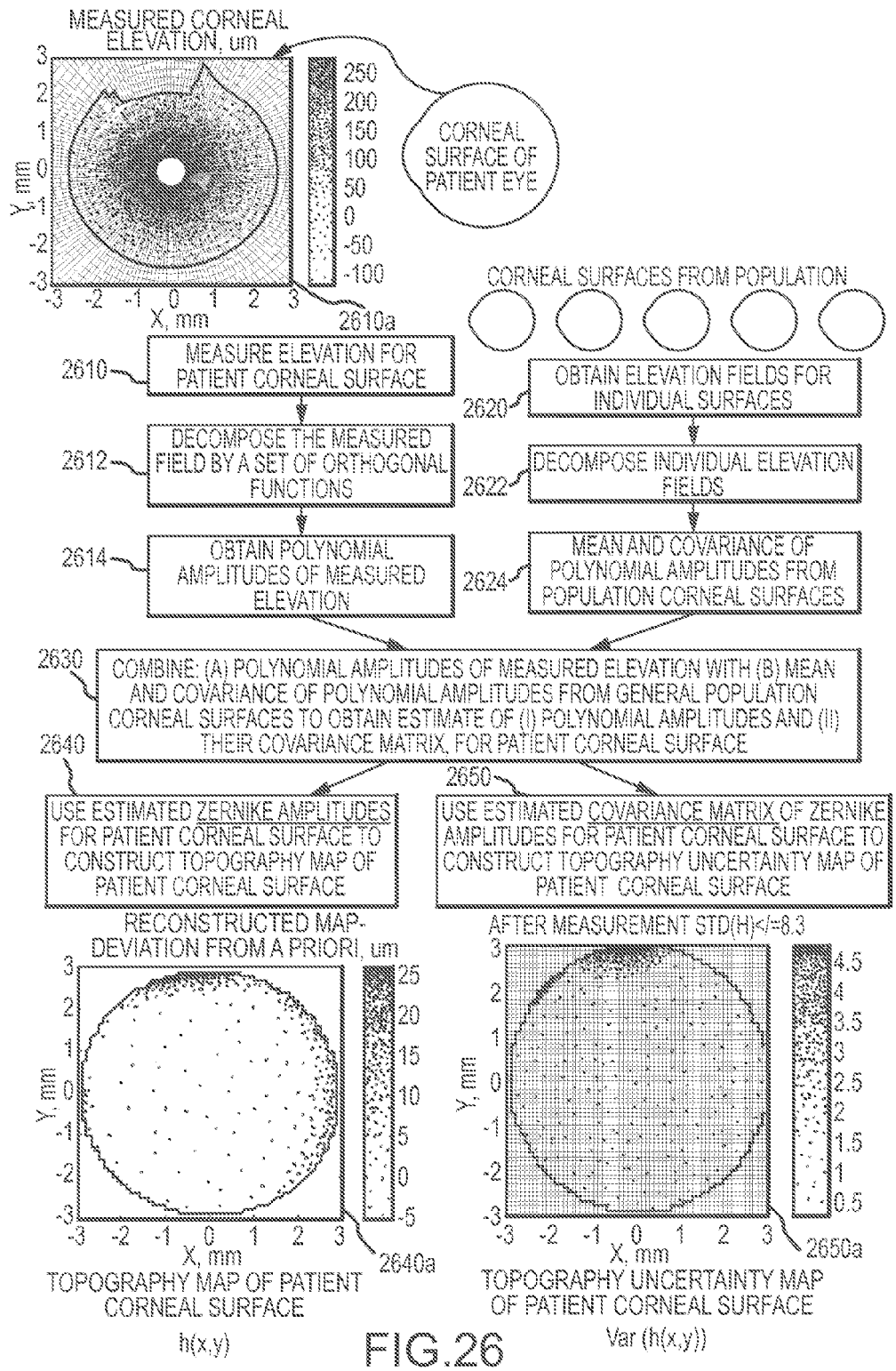
FIGS. 26 to 26H depict aspects of optical tissue evaluation systems and methods according to embodiments of the present invention.
Figure 26A:
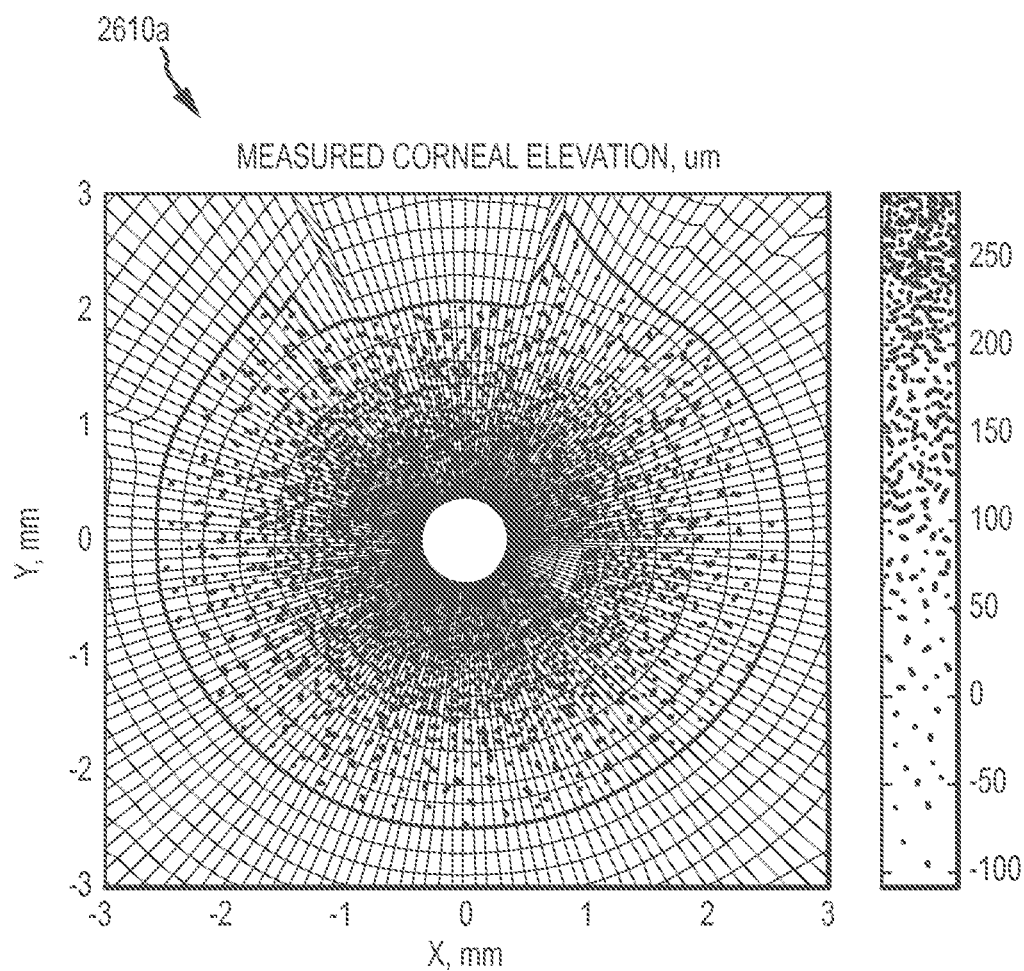

FIG. 26 illustrates aspects of a corneal surface evaluation technique according to embodiments of the present invention. Exemplary methods and systems may involve measuring or obtaining an elevation 2610a for a patient corneal surface, as indicated by step 2610. A more detailed view of a measured corneal elevation or elevation profile 2610a is depicted in FIG. 26A. According to some embodiments, such measurement data can be provided as an elevation field, defined on a set of points $(x_k, y_k)$. In some cases, a topography measurement can provide a two dimensional field of corneal elevations. In some cases, a vector of the measured data or field values can be represented by H. In some instance, the measured data corresponding to the corneal elevation field of a particular patient can be noisy or incomplete. As shown here, a measurement of the corneal elevation field may present gaps, for example (e.g. near the upper central portion of FIG. 26A).

As indicated by step 2612 in FIG. 26, systems and methods may also involve decomposing the measured field by a set of orthogonal functions. Relatedly, techniques may involve determining Zernike amplitudes (e.g. amplitudes for individual terms in a Zernike polynomial expansion) of a measured elevation, as indicated by step 2614. Such measured amplitudes can be further processed, as discussed elsewhere herein.

Figure 26B:
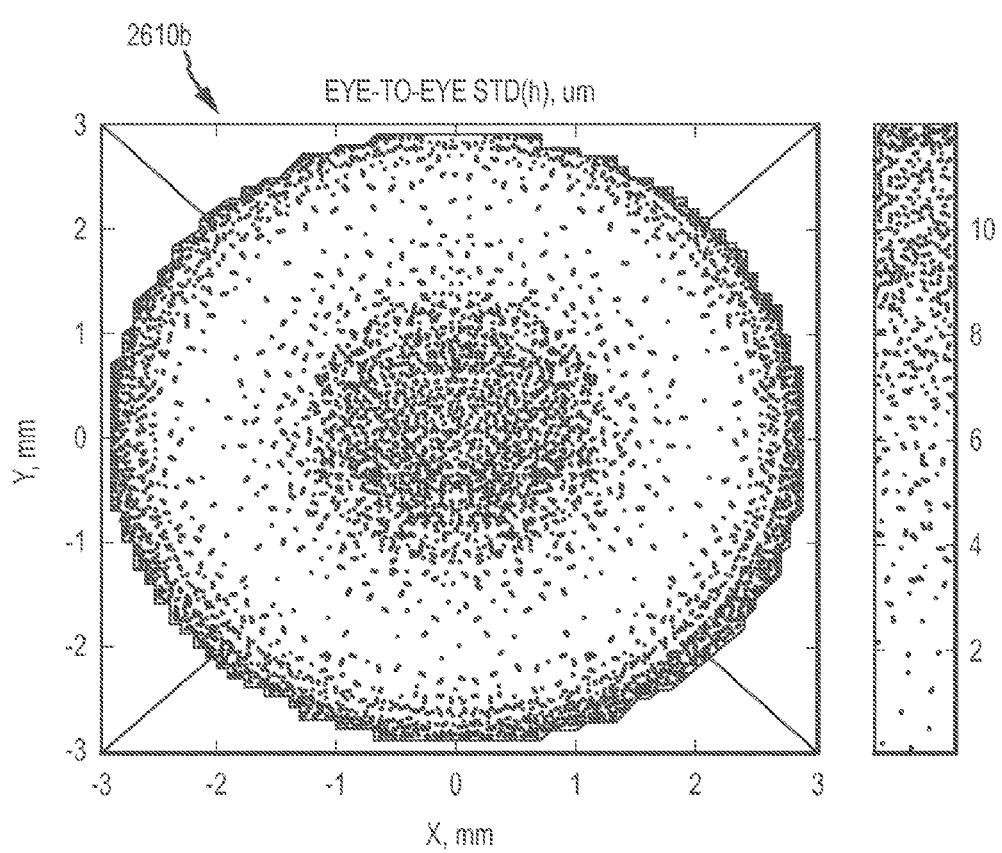
Figure 26C:
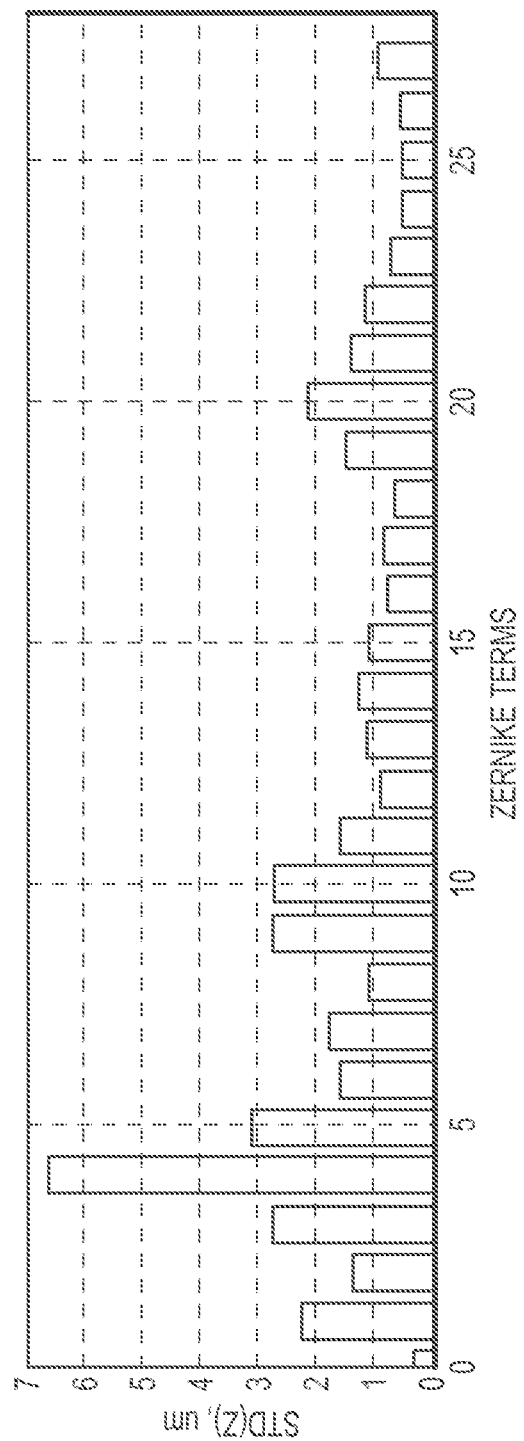
Figure 26D:
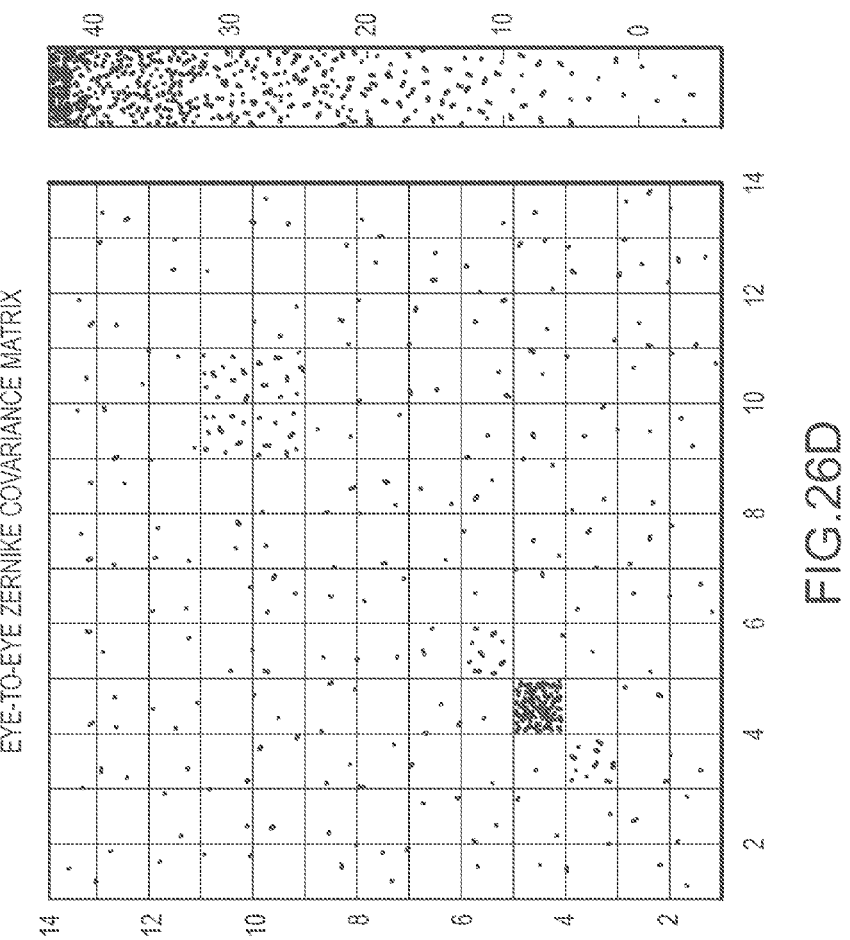

As indicated by step 2620 in FIG. 26, systems and methods may also involve obtaining multiple elevation fields corresponding to individual corneal surfaces, selected from a general population of eyes. The data may be obtained from the general population from any other desired group of eyes. The individual elevation fields may be decomposed by a set of orthogonal functions, as indicated by step 2622. As shown in step 2624, it is possible to obtain mean and covariance information from the decomposed fields. For example, based on the decomposed individual fields, it is possible to determine mean values and a covariance matrix for the general population corneal surfaces. Hence, a priori mean and covariance information for amplitudes of Zernike decomposition results corresponding to corneal topography can be estimated or otherwise determined or obtained from corneal topography measurement data for a general population. FIG. 26B shows an area map 2610b for a priori standard deviation for corneal elevation field (e.g. 6 mm circle) according to embodiments of the present invention. Relatedly, the graph depicted in FIG. 26C shows a priori standard deviation of Zernike amplitudes for corneal elevation field according to embodiments of the present invention. Further, FIG. 26D shows a covariance matrix of Zernike amplitudes for corneal elevation field, according to embodiments of the present invention.

As indicated by step 2630 in FIG. 26, systems and methods may also involve combining polynomial amplitude data (e.g. Zernike amplitudes in step 2614) of a measured elevation of an eye of a patient with mean and covariance amplitude data (e.g. mean and covariance of amplitudes in step 2624) to obtain an estimate of polynomial amplitudes and their covariance matrix for the patient corneal surface. For example, vector data corresponding to a priori mean and a priori covariance matrix information for amplitudes, respectively $A_k^{(prior)}$ and $\hat{M}^{(prior)}$, can constitute input into a Kalman-Bucy filter. Together with such general population input data, a vector H corresponding to measurement data (e.g. topography elevations or associated Zernike amplitudes) for an individual eye of a patient can also be used as input for the Kalman-Bucy filter. The Kalman-Bucy filter can be applied to obtain estimate data for the corneal surface of the eye of the patient, according to the following formulas:

$$A_k = A_k^{(prior)} + \hat{K} \cdot \{\vec{H} - \hat{G} \cdot A \, A_k^{(prior)}\}$$

$$\hat{M} = \hat{K} \cdot \{\hat{I} - \hat{K}\hat{G}\} \cdot \hat{M}^{(prior)}$$

Figure 26E:
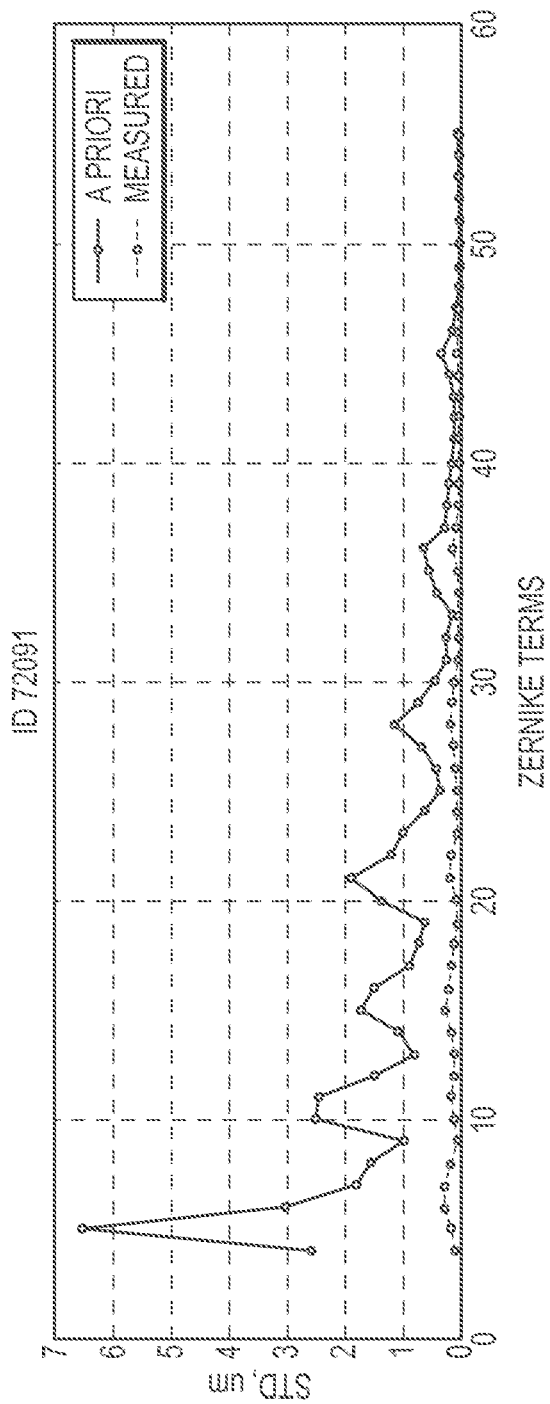
Figure 26F:
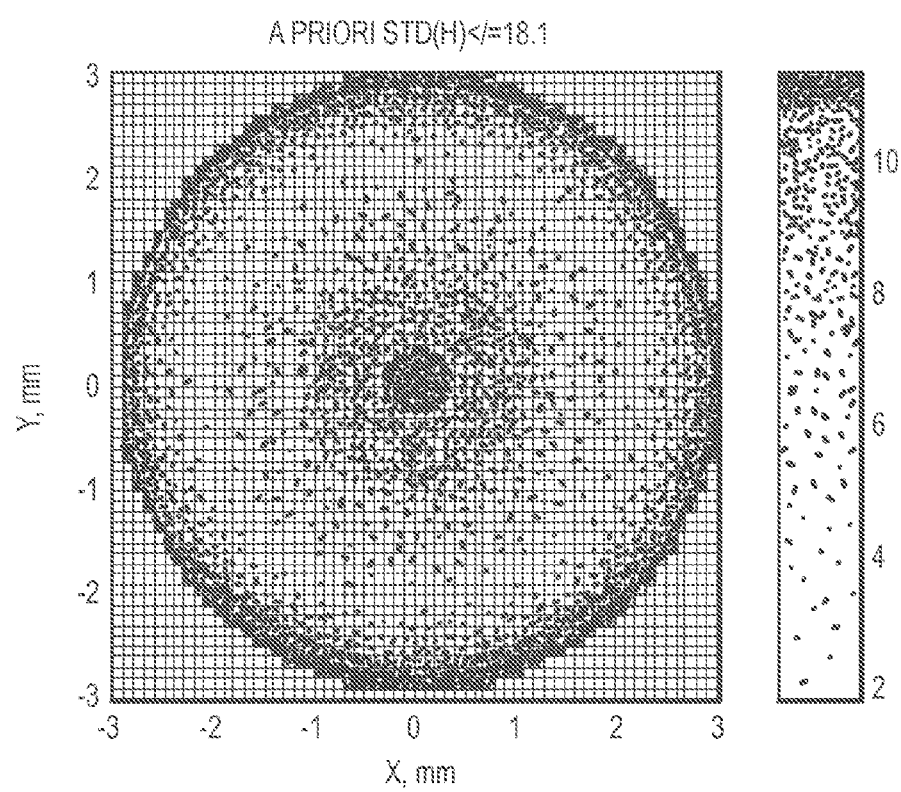

Here, $A_k$ represents an estimate of measured Zernike amplitudes, and $\hat{M}$ represents an estimate of a covariance matrix for the measured Zernike amplitudes. $\hat{G}$ is the operator of surface reconstruction from Zernike amplitudes (a surface defined on $x_i$, $y_i$ points can be computed from Zernike amplitudes and Zernike polynomials $\Phi_k(x_i,y_i)$ at these points as $$S_i = \sum_k A_k \Phi_k(x_i, y_i)\Big)\Big), \; \hat{K} = \hat{M}^{-1} \hat{G}^T \hat{F}$$

is the Kalman-Bucy gain, $\hat{F} = \{\hat{G}\hat{M}^-\hat{G}^T + \hat{N}\}^{-1}$, $\hat{N}$ is the data noise covariance matrix, and $\hat{I}$ is a unitary matrix. Diagonal elements of the estimated covariance matrix, $\hat{M}$, can provide an estimate of uncertainty with regard to the measured amplitudes. FIG. 26E depicts a priori mean values and an example of measured values of Zernike amplitudes for corneal topography elevations, according to embodiments of the present invention. Areas with good measurement coverage can have low uncertainty, and lacunas in measurement can yield high uncertainty data, as defined by a priori variance, as depicted in the a priori elevation uncertainty representation of FIG. 26F.

Figure 26G:
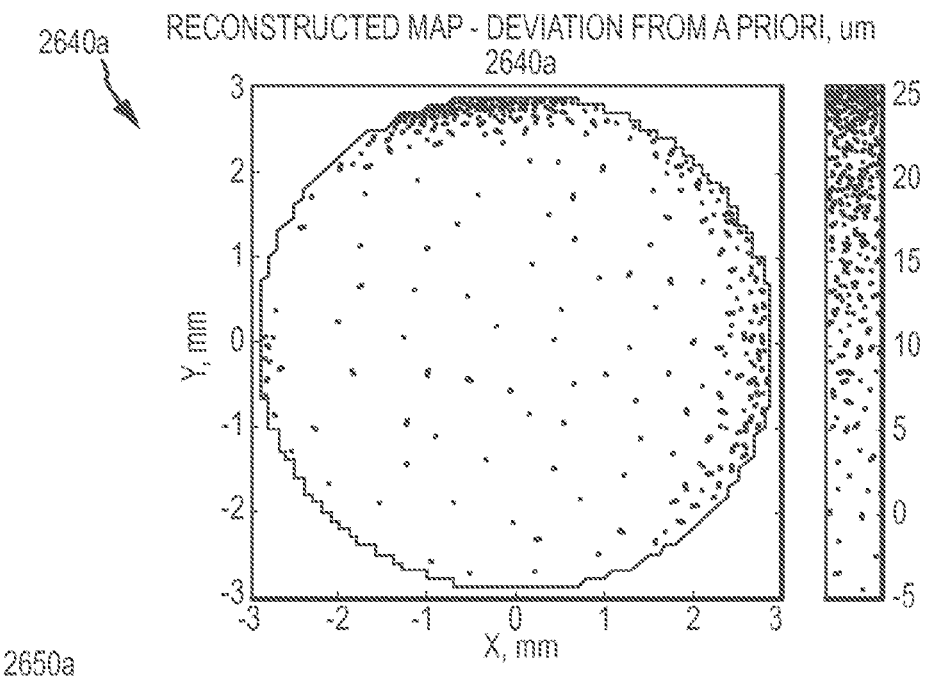
Figure 26H:
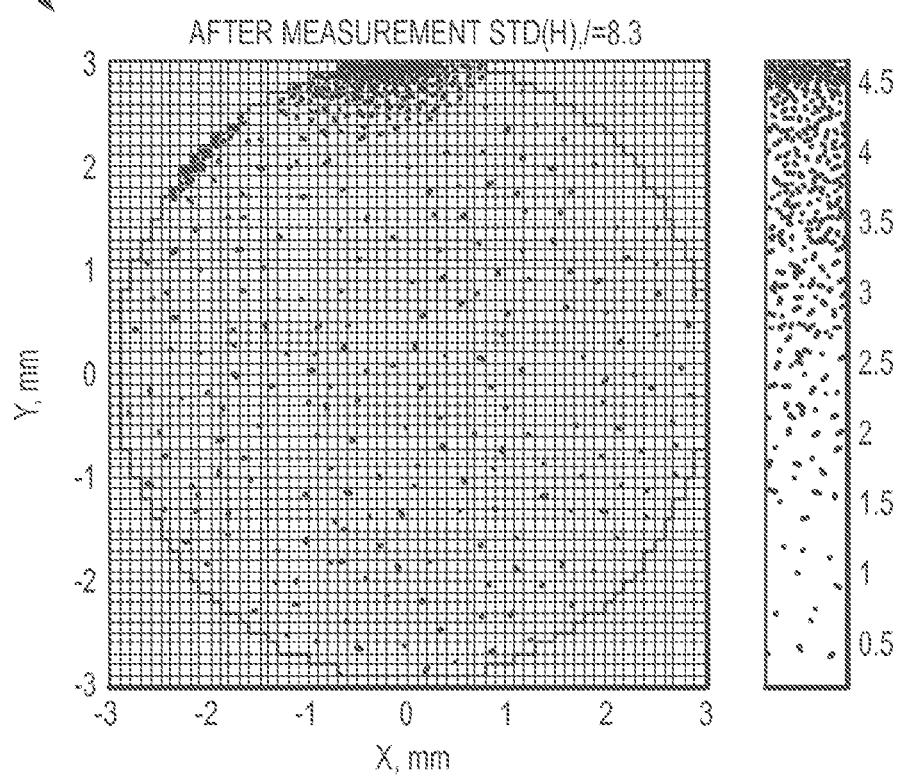

As indicated by step 2640 in FIG. 26, systems and methods may also involve constructing a topography map or topographical representation of the patient corneal surface based on estimated polynomial amplitudes (e.g. $A_k$). A more detailed view of the reconstructed patient corneal surface topography map or elevation area map 2640a is depicted in FIG. 26G. Similarly, as indicated by step 2650, systems and methods may involve constructing a topography uncertainty map or topographical uncertainty representation of the patient corneal surface, based on an estimated covariance matrix (e.g. $\hat{M}$). A more detailed view of the topography measurement uncertainty 2650a is depicted in FIG. 26H.

Hence, as depicted in this example and further discussed elsewhere herein, embodiments of the present invention encompass systems and methods for objective quality estimation for wavefront and corneal topography measurements. In certain instances, ocular wavefront measurements and/or corneal topography measurements may have limited accuracy because measurement data can be noisy, and their coverage area may have gaps. Relatedly, even where a full measured field can be restored, uncertainty may remain in the accuracy of the restored field. For example, areas where the measurement noise is high or where measurement data is missing may provide less reliable data, as compared with areas that contain high quality measurement data coverage. Embodiments of the present invention encompass systems and methods for providing an objective estimate of the measurement quality. For example, embodiments provide for the generation of an uncertainty map which can be compared or correlated with a restored measured field.

Systems and methods for measurement data processing for corneal topography or ocular wavefront applications, whereby such data can be acquired by medical diagnostics devices such as an ocular aberrometer or corneal topographer, can employ conversion of the random measurement data set to a regular two dimensional map by some interpolation scheme or through decomposition of available data into Fourier or orthogonal polynomials with subsequent reconstruction of the two dimensional field from those decompositions. The quality of such reconstruction may contain some amount of uncertainty. Embodiments of the present invention encompass the use of a priori information about measured field parameters for the purposes of reconstruction. For example, field restoration techniques can combine a priori information along with measured field data parameters to achieve improved accuracy for corneal evaluation.

Accordingly, embodiments of the present invention encompass systems and methods for the restoration of a field based on decomposition of a measured field (e.g. which may include noisy and/or incomplete measurement data) by a set of orthogonal functions. In some cases, the amplitudes of these orthogonal functions are estimated, and the entire field may be restored from the decomposition. In some instances, Zernike polynomials can be used. In some cases, a different set of orthogonal polynomials of Fourier decomposition can be used instead of Zernike polynomials. Exemplary techniques can combine a priori information regarding amplitudes (e.g. mean values and covariance matrix) with measured field values on a random set of locations. In some cases, such combinations can be based on a Kalman-Bucy approach. For example, Kalman-Bucy techniques may operate to receive parameters associated with measured pixels and a priori information (e.g. amplitudes mean and covariance matrix) as input. Further, Kalman-Bucy techniques can yield statistically optimal estimates for measured amplitudes and their covariance matrix. The measured field alongside with the variance map can be computed from these estimates. A priori mean amplitudes and their covariance matrix can be determined from available data for a general population.

The techniques described herein are well suited for use with other types of measurement, for example where measurement data are acquired on a random set of points and a field area map is restored from the random measured data. According to some embodiments, the techniques disclosed herein can be applied to wavefront measurements, for example as performed with an aberrometer, where lenslet images of distorted spots yield noisy and incomplete data. According to some related embodiments, Fourier decomposition can be used to reconstruct the wavefront surface. A combination of a priori information and measurement data, for example which can be provided by a Kalman-Bucy approach, can produce an objective estimation of wavefront measurement quality (e.g. variances of Fourier amplitudes and variance area map).

In some instances, embodiments of the present invention encompass systems and method for evaluating the accuracy of wavefront or topographic measurement of an eye of a patient, particularly where such a measurement may involve noisy or incomplete data. Exemplary techniques may involve obtaining measurement data for the eye of the patient, and decomposing the measurement data to obtain amplitude parameter data. Relatedly, techniques may involve obtaining measurement data for a population of eyes, and decomposing that measurement data to obtain amplitude parameter and covariance parameter data. Further, techniques may include combining amplitude data associated with the patient measurement with amplitude parameter data and covariance parameter data associated with the population measurements, so as to obtain estimated amplitude parameter data and estimated covariance parameter data. Estimated amplitude parameter data can be used to construct a representation (e.g. map) of the patient eye, and estimated covariance parameter data can be used to construct an uncertainty representation (e.g. uncertainty map) of the patient eye. The uncertainty representation for the patient eye can be used to evaluate the accuracy of the representation for the patient eye. For example, the uncertainty representation can indicate areas of the patient eye representation where there is high uncertainty, and areas of the patient eye representation where there is low uncertainty.

For example, a method of evaluating the accuracy of a topographical representation of a patient eye may involve measuring an elevation for a corneal surface, and combining the measured elevation with a priori corneal surface information to provide an estimate of mean and covariance of measured Zernike amplitudes associated with the corneal surface. The a priori corneal surface information can include a plurality of mean and covariance of Zernike amplitudes associated with the statistics of corneal surfaces for general population known independently of the measured patient cornea elevation. Further, the method may include constructing a corneal topography map based on the estimates of the Zernike amplitudes, and constructing a corneal topography uncertainty map based on estimated covariance. Relatedly, the method may include evaluating the accuracy of the reconstructed corneal topography map based on the corneal topography uncertainty map. For example, the uncertainty map can indicate areas of the reconstructed patient eye topography map where there is high uncertainty, and areas of the reconstructed patient eye topography map where there is low uncertainty.

While the above provides a complete and accurate description of specific embodiments of the invention, several changes and adaptations of the present invention may be readily made. For example, while specific reference has been made to ablating predetermined shapes based on pre-operative measurements, systems and methods of the present invention are applicable to any ablation, for example ablation based on intra-operative measurements. While specific reference has been made to correcting optical aberrations made with refractive, wavefront and topography measurements, methods and systems of the present invention can be used to ablate any desired shape in tissue based on any measurement. While specific reference has been made to using Zernike polynomials with Kalman-Bucy technique, a different set of orthogonal polynomials of Fourier decomposition may be used in place of Zernike polynomials.

The methods and apparatuses of the present invention may be provided in one or more kits for such use. The kits may comprise a system for evaluating a corneal surface, such as a corneal surface of an eye, and instructions for use. Optionally, such kits may further include any of the other system components described in relation to the present invention and any other materials or items relevant to the present invention. The instructions for use can set forth any of the methods as described herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of evaluating a topography of a corneal surface of an eye of a patient, the method comprising:
   measuring a topography elevation field for the patient eye corneal surface;
   determining a measured Zernike amplitude profile for the patient eye based on the topography elevation field;
   combining the measured Zernike amplitude profile with a priori corneal surface information to provide an estimated Zernike amplitude profile and an estimated Zernike amplitude covariance matrix for the patient eye, the a priori corneal surface information comprising mean and covariance Zernike amplitude profiles associated with multiple corneal surfaces of a general population;
   constructing a corneal topography map for the patient based on the estimated Zernike amplitude profile;
   constructing a corneal topography uncertainty map for the patient based on the estimated Zernike covariance matrix; and
   evaluating the patient corneal surface topography based on the corneal topography map and the corneal uncertainty map.

2. The method according to claim 1, wherein the measured Zernike amplitude profile for the patient eye is determined by decomposing the topography elevation field of the patient eye corneal surface into a Zernike series representation.

3. The method according to claim 1, where the a priori corneal surface information is obtained by:
   acquiring individual topography elevation fields corresponding respectively to individual eyes of the general population;
   decomposing the individual topography elevation fields into corresponding Zernike series representations;
   evaluating a mean and a variance of amplitudes of the Zernike series representations; and
   preparing the a priori information from the mean and the variance of amplitudes of the Zernike series representations.

4. The method of claim 1, wherein the combining step comprises inputting the a priori information into a Kalman-Bucy filter together with the measured Zernike amplitude profile.

5. The method of claim 4, wherein the inputting step comprises applying the Kalman-Bucy filter according to:

$$A_k = A_k^{(prior)} + \hat{K} \cdot \{\vec{H} - \hat{G} \cdot A_k^{(prior)}\}$$

$$\hat{M} = \hat{K} \cdot \{\hat{I} - \hat{K}\hat{G}\} \cdot \hat{M}^{(prior)}$$

wherein $A_k$ corresponds to the estimated Zernike amplitude profile for the patient eye, $A_k^{(prior)}$ corresponds to the a priori mean Zernike amplitude profile associated with the multiple general population corneal surfaces, $\hat{K}$ represents a Kalman-Bucy gain, $\vec{H}$ corresponds to a vector of the measured elevation field for the patient eye corneal surface, and $\hat{G}$ is an operator of surface reconstruction from the Zernike amplitudes, and
wherein $\hat{M}$ corresponds to the estimated Zernike amplitude covariance matrix for the patient eye, $\hat{I}$ is a unitary matrix, and $\hat{M}^{(prior)}$ corresponds to the a priori covariance Zernike amplitude profile associated with the multiple general population corneal surfaces.

6. A method of planning a refractive correction treatment for an eye of a patient, the method comprising:
   obtaining a measured Zernike amplitude profile for the patient eye, the measured Zernike amplitude profile based on a measured topography elevation field for a corneal surface of the patient eye;
   combining the measured Zernike amplitude profile with a priori corneal surface information to provide an estimated Zernike amplitude profile and an estimated Zernike amplitude covariance matrix for the patient eye, the a priori corneal surface information comprising a mean and covariance Zernike amplitude profiles associated with multiple corneal surfaces of a general population;
   constructing a corneal topography uncertainty map for the patient based on the estimated Zernike covariance matrix;
   constructing a corneal topography map for the patient based on the estimated Zernike amplitude profile and the corneal topography uncertainty map;
   determining ablation properties locally across the corneal surface of the patient eye based on the corneal topography map; and
   formulating a treatment plan using the ablation properties by adjusting a first virtual ablation shape to form a second virtual ablation shape, the first virtual shape representing a depth of material to be removed from a treatment area to form a desired shape, the second virtual shape being formed from the first virtual shape in response to the corneal topography map.

7. A method of treating a cornea of a patient eye with a laser beam, the method comprising:
   obtaining a measured Zernike amplitude profile for the patient eye, the measured Zernike amplitude profile based on a measured topography elevation field for a corneal surface of the patient eye;
   combining the measured Zernike amplitude profile with a priori corneal surface information to provide an estimated Zernike amplitude profile and an estimated Zernike amplitude covariance matrix for the patient eye, the a priori corneal surface information comprising mean and covariance Zernike amplitude profiles associated with multiple corneal surfaces of a general population;
   constructing a corneal topography uncertainty map for the patient based on the estimated Zernike covariance matrix;
   constructing a corneal topography map for the patient based on the estimated Zernike amplitude profile and the corneal topography uncertainty map;
   mapping angles between the corneal surface and the laser beam over a treatment area;

determining ablation properties locally across the treatment area in response to the mapped angles;

formulating a treatment plan using the ablation properties by adjusting a first virtual ablation shape to form a second virtual ablation shape, the first virtual shape representing a depth of material to be removed from the treatment area to form a desired shape, the second virtual shape being formed from the first virtual shape in response to the mapped angles; and ablating the treatment area according to the treatment plan to form the desired shape in the corneal surface.

8. The method according to claim 7, wherein the desired shape is based at least in part on a result of a measurement selected from the group consisting of an aberration measurement of the eye, a refractive measurement of the eye, and a topography measurement of the eye.

9. A system for treating a corneal surface of a patient eye with a laser beam, the eye having a refractive defect, wherein a desired refractive correcting shape mitigates the refractive defect, the system comprising:

a laser emitting a beam of an ablative light energy; and at least one processor coupled to the laser beam and having a computer program, the computer program embodying instructions for:

combining a measured Zernike amplitude profile for the patient eye with a priori corneal surface information to provide an estimated Zernike amplitude profile and an estimated Zernike amplitude covariance matrix for the patient eye, the a priori corneal surface information comprising mean and covariance Zernike amplitude profiles associated with multiple corneal surfaces of a general population, and the measured Zernike amplitude profile for the patient eye based on a measured topography elevation field of the patient eye corneal surface;

constructing a corneal topography uncertainty map for the patient based on the estimated Zernike covariance matrix;

constructing a corneal topography map for the patient based on the estimated Zernike amplitude profile and the corneal topography uncertainty map;

determining ablation properties locally across the corneal surface of the patient eye based on the corneal topography map;

formulating a treatment plan using the ablation properties by adjusting a first virtual ablation shape to form a second virtual ablation shape, the first virtual shape representing a depth of material to be removed from a treatment area to form a desired shape, the second virtual shape being formed from the first virtual shape in response to the corneal topography map; and controlling an ablative treatment using the treatment plan from the second virtual shape so that the treatment forms the desired refractive correcting shape in the surface.

10. A method of evaluating an optical tissue of an eye, the method comprising:

combining a measured orthogonal polynomial amplitude profile for the patient eye with a priori optical tissue information to provide an estimated orthogonal polynomial amplitude profile and an estimated orthogonal polynomial amplitude covariance matrix for the patient eye, the a priori optical tissue information comprising mean and covariance orthogonal polynomial amplitude profiles associated with multiple optical tissue measurements of a general population, and the measured orthogonal polynomial amplitude profile for the patient eye based on a measured topography elevation field of the patient eye corneal surface;

constructing an optical tissue uncertainty map for the patient based on the estimated orthogonal polynomial covariance matrix, the uncertainty map representing a measure of measurement quality; and evaluating the optical tissue of the patient eye based on the estimated orthogonal polynomial amplitude profile and the optical tissue uncertainty map.

11. The method according to claim 10, wherein the measured orthogonal polynomial amplitude profile for the patient eye is based on a measurement selected from the group consisting of a corneal surface topography measurement of the eye and a wavefront measurement of the eye.

12. A method for evaluating the accuracy of an optical tissue measurement of an eye of a patient, the method comprising:

obtaining amplitude data corresponding to the optical tissue measurement of the patient eye, the amplitude data based on a measured topography elevation field for a corneal surface of the patient eye;

obtaining amplitude data and covariance data corresponding to optical tissue measurements of multiple eyes of a population;

combining the amplitude data corresponding to the patient measurement with the amplitude data and covariance data corresponding to the population measurements, so as to obtain estimated amplitude data and estimated covariance data;

constructing a representation of the patient optical tissue based on the estimated amplitude data;

constructing an uncertainty representation of the patient optical tissue based on the estimated covariance data; and evaluating the accuracy of the optical tissue measurement based on the representation of the patient optical tissue and the uncertainty representation of the patient optical tissue.

* * * * *